US009085698B2

(12) United States Patent
Romanov et al.

(10) Patent No.: US 9,085,698 B2
(45) Date of Patent: Jul. 21, 2015

(54) DYES FOR LABELLING MOLECULAR LIGANDS

(75) Inventors: Nikolai Romanov, Nr Saffron Walden (GB); Carole Anastasi, Nr Saffron Walden (GB); Xiaohai Liu, Nr Saffron Walden (GB)

(73) Assignee: Illumina Cambridge Limited, Nr. Saffron Walden (GB)

( * ) Notice: Subject to any disclaimer, the term of this patent is extended or adjusted under 35 U.S.C. 154(b) by 0 days.

(21) Appl. No.: 14/346,657

(22) PCT Filed: Sep. 23, 2011

(86) PCT No.: PCT/EP2011/004779
§ 371 (c)(1),
(2), (4) Date: Jun. 16, 2014

(87) PCT Pub. No.: WO2013/041117
PCT Pub. Date: Mar. 28, 2013

(65) Prior Publication Data
US 2014/0323741 A1 Oct. 30, 2014

(51) Int. Cl.
*C07D 403/06* (2006.01)
*C09B 23/06* (2006.01)
*C09B 23/08* (2006.01)
*C09B 23/12* (2006.01)
*C09B 23/02* (2006.01)
*C09B 23/10* (2006.01)

(52) U.S. Cl.
CPC .............. *C09B 23/12* (2013.01); *C07D 403/06* (2013.01); *C09B 23/02* (2013.01); *C09B 23/06* (2013.01); *C09B 23/08* (2013.01); *C09B 23/083* (2013.01); *C09B 23/10* (2013.01)

(58) Field of Classification Search
USPC .............................................. 548/305.7, 455
See application file for complete search history.

(56) References Cited

U.S. PATENT DOCUMENTS

| 6,159,673 | A | 12/2000 | Nishigaki et al. |
| 6,238,838 | B1 * | 5/2001 | Gaschler et al. ........... 430/278.1 |
| 6,291,203 | B1 * | 9/2001 | Poot et al. .................... 435/40.5 |
| 6,348,599 | B1 * | 2/2002 | Cummins et al. ............. 548/455 |
| 8,809,551 | B1 | 8/2014 | Romanov et al. |
| 2008/0044352 | A1 | 2/2008 | Beletskii et al. |
| 2012/0088262 | A1 | 4/2012 | Dehghani et al. |

FOREIGN PATENT DOCUMENTS

| EP | 1792949 | | 12/2006 |
| EP | 2130875 | | 12/2009 |
| EP | 2251380 | | 11/2010 |
| GB | 1020295 | | 2/1966 |
| JP | 03-105338 | A * | 5/1991 |
| JP | 06-332104 | A * | 12/1994 |
| JP | 2002226731 | | 8/2002 |
| SU | 432166 | | 6/1974 |
| WO | 9940223 | A1 | 8/1999 |
| WO | 2005014723 | | 2/2005 |
| WO | 2005/044923 | | 5/2005 |
| WO | 2010/121163 | | 10/2010 |
| WO | 2013041117 | | 3/2013 |

OTHER PUBLICATIONS

An English translation of JP 06-332104 (Meji et al.), 1994.*
Moss et al., Pure & Applied Chemistry, 1995, vol. 67, No. 8/9, pp. 1307, 1367-1370.*
Kawashima et al., CA 116:31272, 1992.*
Meji et al., CA 122:201115, 1995.*
Chemical Abstract Registry No. 161800-75-5, indexed in the Registry file on STN CAS Online Mar. 30, 1995.*
An English translation of Kawashima et al., JP 03-105338 A, 1991.*
"International Search Report and Written Opinion", PCT/EP2013/054783, Apr. 23, 2013, 17 pages.
Lekoev, et al., "Photographic properties of some symmetrical carbocyanine dyes with different alkyl groups on the nitrogen of the heterocyclic groups", retrieved from STN accession No. 1959:104271; Database accession No. 53:104271 & Zhurnal Nauchnoi I Prikladnoi Fotografii I Kinematografii, vol. 3, 1958, 419-426.

* cited by examiner

*Primary Examiner* — Laura L. Stockton
(74) *Attorney, Agent, or Firm* — Jones Day

(57) ABSTRACT

Cyanine dyes with improved fluorescence intensity and photostability.

9 Claims, 3 Drawing Sheets

DYES FOR LABELLING MOLECULAR LIGANDS

This application is a national phase entry pursuant to 35 U.S.C. §371 of International Application No. PCT/EP2011/004779, which has the international filing date of Sep. 23, 2011, which is incorporated herein by reference in its entirety.

BACKGROUND OF THE INVENTION

The present invention relates generally to fluorescent dye reagents.

Fluorescent dyes are widely used for labeling, detecting, and quantifying components in a sample. Analytical methods that utilize such dye reagents include fluorescence microscopy, fluorescence immunoassay, flow cytometric analysis of cells, and various other applications. The choice of fluorescent dyes is particularly important in applications that utilize multiplex, multicolor analysis.

Many fluorescent dyes currently used in aqueous systems have a tendency to form dimers or aggregate compromising their performance. Moreover, many dyes in current use exhibit poor chemical and/or photochemical stability. Thus, there is a continued need for the development of new fluorescent dye compounds. The present invention satisfies this need and provides related benefits as well.

SUMMARY OF THE INVENTION

In some aspects, embodiments disclosed herein relate to a compound of formula I:

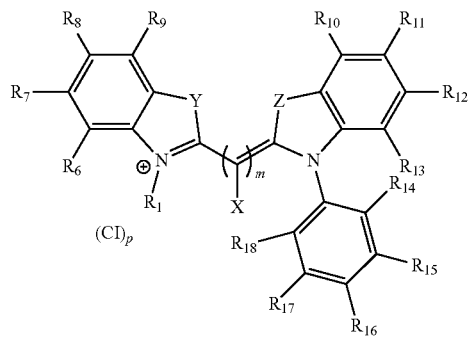

wherein
Cl is a charge balancing counterion and p is an integer from 1-7;
m is 1, 3, 5, 7, or 9;
each incidence of X is independently hydrogen, halogen, alkyl- or aryloxy, alkyl- or arylthio, amino- or substituted amino, aryl or alkyl, any of which may be optionally substituted with a substituent selected from carboxyl, sulfonate, sulfinate, sulfoxide, sulfone, sulfonamide, hydroxyl, amino, alkylamino, dialkylamino, alkoxy, and halogen; optionally, one or more X groups are combined to form a carbocyclic ring;
Y is independently selected from O, $NR_a$, S, Se, $CR_b$=CR, and $CR_2R_3$;
Z is independently selected from O, $NR_a$, S, Se, $CR_b$=CR, and $CR_4R_5$;
wherein $R_a$, $R_b$, $R_c$, $R_2$, $R_3$, $R_4$, and $R_5$ are independently selected from alkyl, aryl or substituted alkyl (such as aminoallyl), carboxyalkyl, sulfoalkyl or substituted aryl (such as carboxyaryl or sulfoaryl);
$R_1$ is selected from aryl (for example phenyl, naphthyl), aralkyl or alkyl, any of which may be optionally substituted with at least one substituent selected from carboxyl, sulfonate, sulfinate, sulfoxide, sulfone, sulfonamide, hydroxyl, amino, alkyl(aryl)amino, dialkyl(aryl)amino, alkoxy, aryloxy, halogen, succinimidyl ester, ester, and amide, mono- or disubstituted amide;
$R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ are independently selected from carboxyl, sulfonate, sulfinate, sulfoxide, sulfone, sulfonamide, hydroxyl, amino, alkylamino, dialkylamino, alkoxy, halogen, alkyl succinimidyl ester, ester, amide, or any ortho-disposed pair of $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ is combined to form a further fused aromatic or heterocyclic ring which is optionally substituted; wherein at least one of $R_{14}$, $R_{15}$, $R_{16}$, $R_{17}$, or $R_{18}$ is sulfonate or a further fused aromatic ring derived from $R_{14}$, $R_{15}$, $R_{16}$, $R_{17}$, or $R_{18}$ comprises at least one sulfonate substituent; with the proviso that none of $R_{14}$, $R_{15}$, $R_{16}$, $R_{17}$, and $R_{18}$ are carboxyl.

In other aspects, embodiments disclosed herein relate to a method of making the aforementioned compounds of formula I. The method includes condensing a compound comprising formula IIA or IIB:

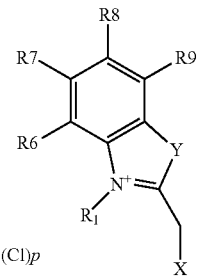

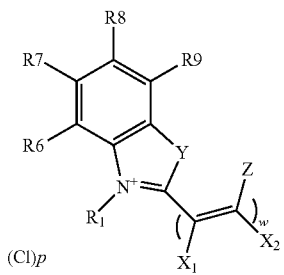

wherein Z=OR, SR, NHR or NR; w=0, 1, 2, 3
with a compound comprising formula IIIA or IIIB appropriately:

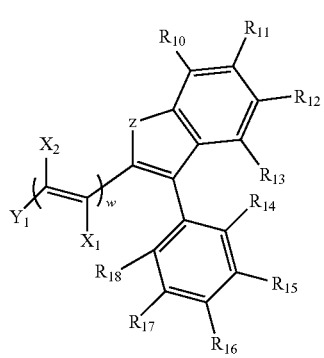

-continued

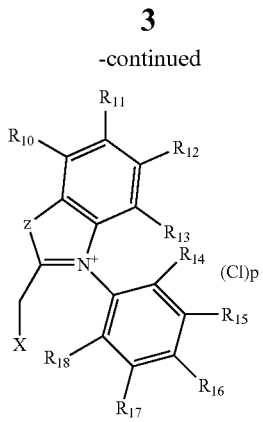
IIIB wherein $Y_1$ is NHR, $NR_dR_e$, or $XR_o$, (where X=O, S); w is 1, 2 or 3.

To improve yield of unsymmetrical dye structure I from starting materials IIA and IIIB, synthesis may achieved by a two-step reaction with preliminary formation of hemicyanines IIB and IIIA.

DETAILED DESCRIPTION OF THE INVENTION

Figure 1:
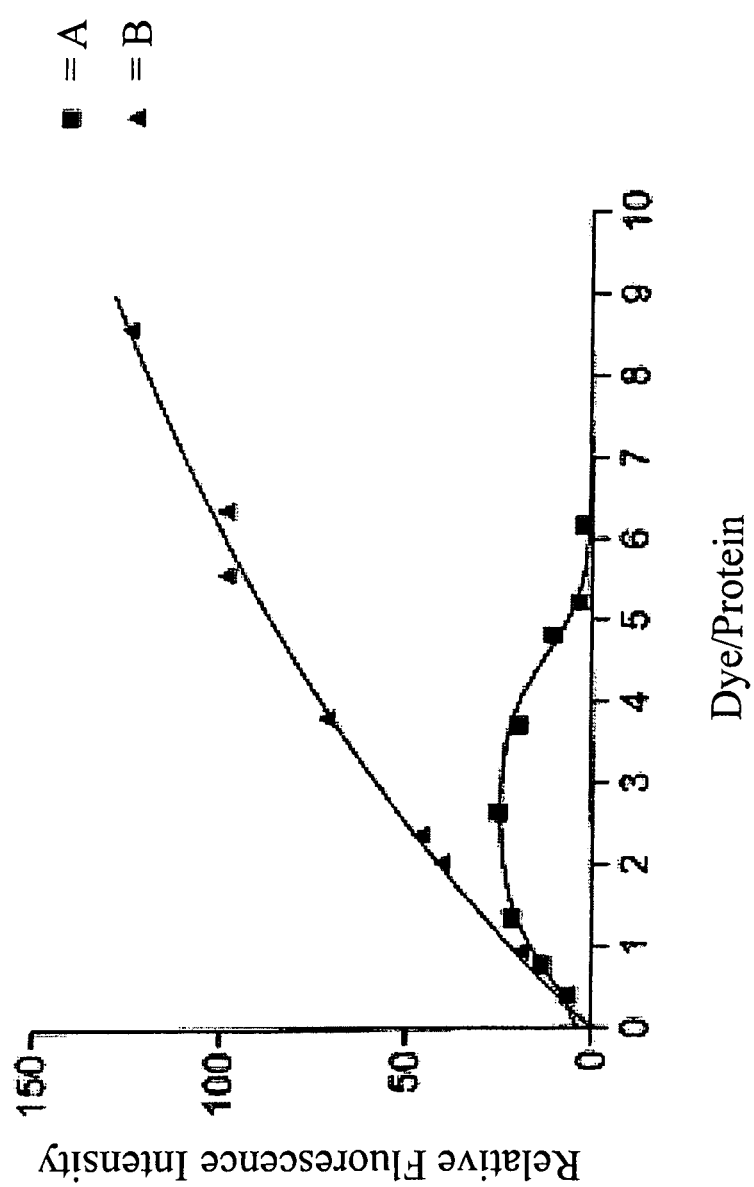
FIG. 1 shows a graph comparing the fluorescent intensities of exemplary dyes A and B with increasing dye/protein ratio.

The present invention is directed, in part, to a fluorescent dye compound of formula I:

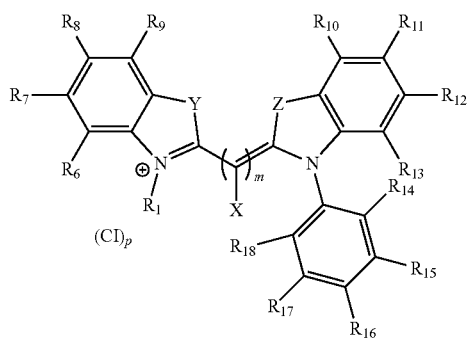
I wherein
Cl is a charge balancing counterion and p is an integer from 1-7;
m is 1, 3, 5, 7, or 9;
each incidence of X is independently hydrogen, halogen, alkyl- or aryloxy, alkyl- or arylthio, amino- or substituted amino, aryl or alkyl, any of which may be optionally substituted with a substituent selected from carboxyl, sulfonate, sulfinate, sulfoxide, sulfone, sulfonamide, hydroxyl, amino, alkylamino, dialkylamino, alkoxy, and halogen; optionally, one or more X groups are combined to form a cyclic ring;
Y is independently selected from O, $NR_a$, S, Se, $CR_b$=CR, and $CR_2R_3$;

Z is independently selected from O, $NR_a$, S, Se, $CR_b$=$CR_c$ and $CR_4R_5$; Wherein $R_a$, $R_b$, $R_c$, $R_2$, $R_3$, $R_4$, and $R_5$ are independently selected from alkyl, aryl or substituted alkyl like aminoallyl, carboxyalkyl, sulfoalkyl; substituted aryl like carboxyaryl, sulfoaryl $R_1$ is selected from aryl (for example phenyl, naphthyl), or alkyl, any of which may be optionally substituted with at least one substituent selected from carboxyl, sulfonate, sulfinate, sulfoxide, sulfone, sulfonamide, hydroxyl, amino, alkyl(aryl)amino, dialkylamino, alkoxy, aryloxy, halogen, succinimidyl ester, ester, and unsubstituted mono- or disubstituted amide;

$R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ are independently selected from carboxyl, sulfonate, sulfinate, sulfoxide, sulfone, sulfonamide, hydroxyl, amino, alkyl(aryl)amino, dialkylamino, alkoxy, aryloxy, halogen, alkyl succinimidyl ester, ester, amide, or any ortho-disposed pair of $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ is combined to form a further fused aromatic or heterocyclic ring which is optionally substituted; wherein at least one of $R_{14}$, $R_{15}$, $R_{16}$, $R_{17}$, or $R_{18}$ is sulfonate or a further fused aromatic ring derived from $R_{14}$, $R_{15}$, $R_{16}$, $R_{17}$, or $R_{18}$ comprises at least one sulfonate substituent; with the proviso that none of $R_{14}$, $R_{15}$, $R_{16}$, $R_{17}$, and $R_{18}$ are carboxyl.

Fluorescent dyes of the invention can be used as markers in many different ways for the analysis of a major part of clinically, biologically, biochemically or chemically relevant substances, such as for example cells, antibodies, proteins, hormones, nucleic acids, oligonucleotides, naturally occurring or modified nucleotides, carbohydrates and some others.

Fluorescent dyes are known to be particularly suitable for biological applications in which highly sensitive detection is needed. Polymethine dyes derivatives often possess very narrow and intense absorption bands; their extinction coefficients and fluorescence quantum yields usually higher than those of other types of dyes having comparable absorption maximum. Moreover, such derivatives possess high sensitivity to their molecular environment, have greater selective absorption and better photostability, which are important parameters, especially for single molecular analysis.

Some indodicyanine dyes exhibit strong fluorescence and high photostability. However, their utility is limited when the cyanine dyes are employed in aqueous solution due, in part, to the tendency to form aggregates [Angew. Chem. 49 (1936) 563; Nature 138 (1936) 1009]. These polymeric dye systems, in contrast with the individual molecule, exhibit a markedly changed absorption and fluorescence behaviour. As a result of the aggregation, the absorption maximum may be shifted in comparison with the monomer dye molecule and more significantly they fluoresce much more poorly.

In some aspects, the present invention provides new cyanine dyes which do not exhibit the aforementioned drawbacks and which in particular exhibit a low tendency towards aggregation of the dyes themselves and are suitable for application as optical and especially fluorescent labels in the visible or near infrared region. In some embodiments, polymethine dyes of the present invention, due to specific substituent placement in dye molecule possess strong fluorescence, very low tendency to form dimers or higher aggregates and possess very high photo—and chemical stability. Due to specific structure of new dyes, they exhibit higher fluorescence and selectivity of light absorption and increased photo—and chemical stability relative to dyes of the same structural class. Higher fluorescence and increased photo—and chemical stability of new dyes are demonstrated below in the Examples.

Without being bound by theory, the N-aryl substituents are believed to provide the dye molecule improved rigidity in terms of intramolecular vibronic interactions; prevent from intermolecular interactions, including reciprocal action with solvents, oxygen and other molecules, resulting in lower non-radiating energy loss from the excited state of such type of cyanine dyes in solution.

Negatively charged dyes of the invention can be prepared with up to eight sulfonic groups in one dye molecule shown below:

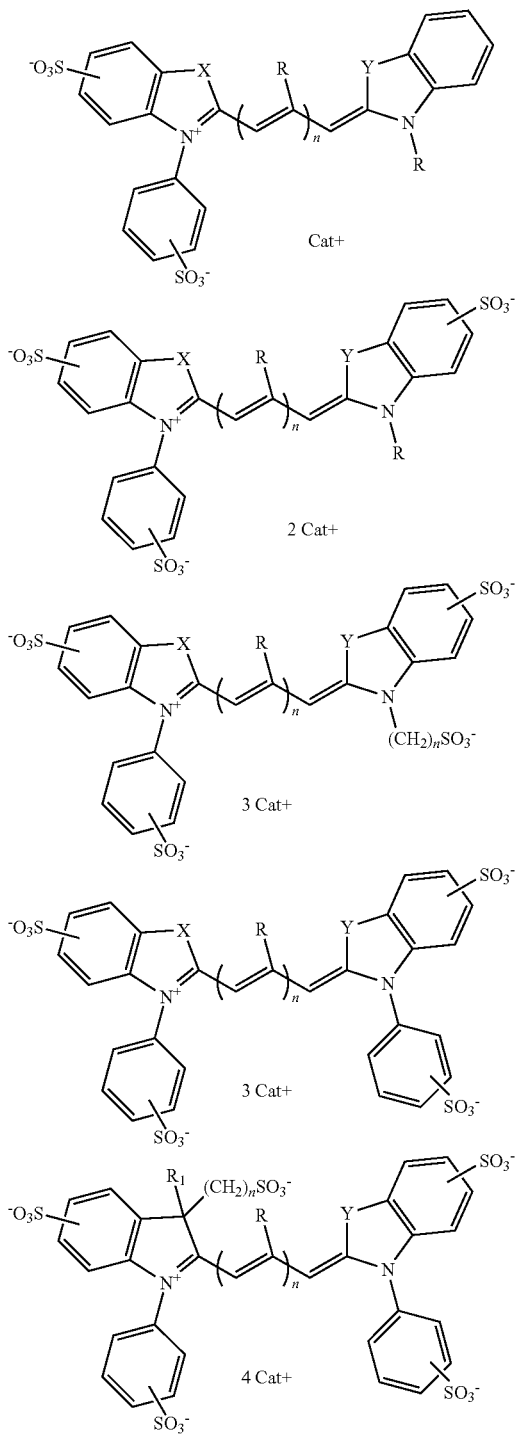

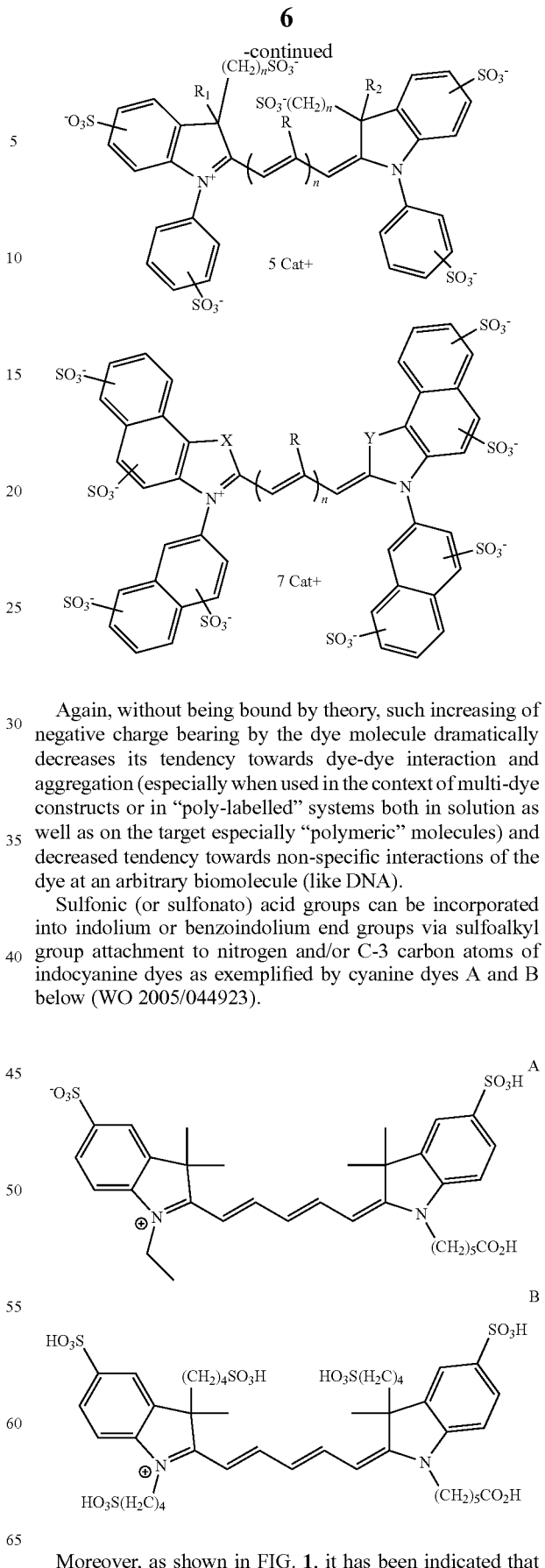

Again, without being bound by theory, such increasing of negative charge bearing by the dye molecule dramatically decreases its tendency towards dye-dye interaction and aggregation (especially when used in the context of multi-dye constructs or in "poly-labelled" systems both in solution as well as on the target especially "polymeric" molecules) and decreased tendency towards non-specific interactions of the dye at an arbitrary biomolecule (like DNA).

Sulfonic (or sulfonato) acid groups can be incorporated into indolium or benzoindolium end groups via sulfoalkyl group attachment to nitrogen and/or C-3 carbon atoms of indocyanine dyes as exemplified by cyanine dyes A and B below (WO 2005/044923).

Moreover, as shown in FIG. 1, it has been indicated that negatively charged dye A having two sulfonate groups is more readily self-quenched with increasing dye concentration relative to dye B with six sulfonic groups.

In the present invention, hydrophilic negatively charged sulfonic-, sulfonato-groups are disposed on aromatic groups in compounds of Formula 1. Without being bound by theory, the out-of-plane twist of the N-phenyl substituent and the presence of a solvent sphere "around" the negatively charged sulfonate group act synergistically to decrease the tendency towards dye-dye interaction and aggregation resulting in the observed fluorescence in water solution, as shown in the Examples below. The 1-phenyl substituent in heterocyclic dye 3H-indolium end-group (N-Aryl) is not planar relative to the rest of dye molecule and thus provides a steric barrier to dye aggregation as well as aggregation with other non-dye molecules. This property can be useful, for example, in applications that employ dyes in conjunction with nucleic acids or proteins, where dye-nucleic or dye-protein interactions can be significant.

By contrast N-alkyl substituted dyes known in the art do not provide such effect. Moreover from space-filling models of fragments of dyes of formula 1, one can observe that introducing a 1-phenyl substituent in heterocyclic dye 3H-indolium end groups (with an additional hydrophilic sulfonic group) increases the solvent surface around the molecule, which is further expected to deteriorate dye-dye interaction and aggregation in water solution and also additionally decrease the tendency towards non-specific interactions of the dye at an arbitrary biomolecule (like DNA) or surface. From a prototype dye based on N-methyl substituted indolium derivatives (like commercial dyes) and based on new N-aryl substituted indolium derivatives, one can observe how significantly decreased ability of the dye molecule to aggregate from even one end-group (N-phenyl substituted) compare to the other (N-methyl).

In some embodiments, dye compounds of the invention exhibit enhanced photostability. It has been indicated that interaction of a dye molecule with oxygen ($O_2^*$) or perhydroxy (OOH) radicals are the predominant pathways for dye photo-degradation. Identification of products of such type reactions have been demonstrated as shown in the scheme below:

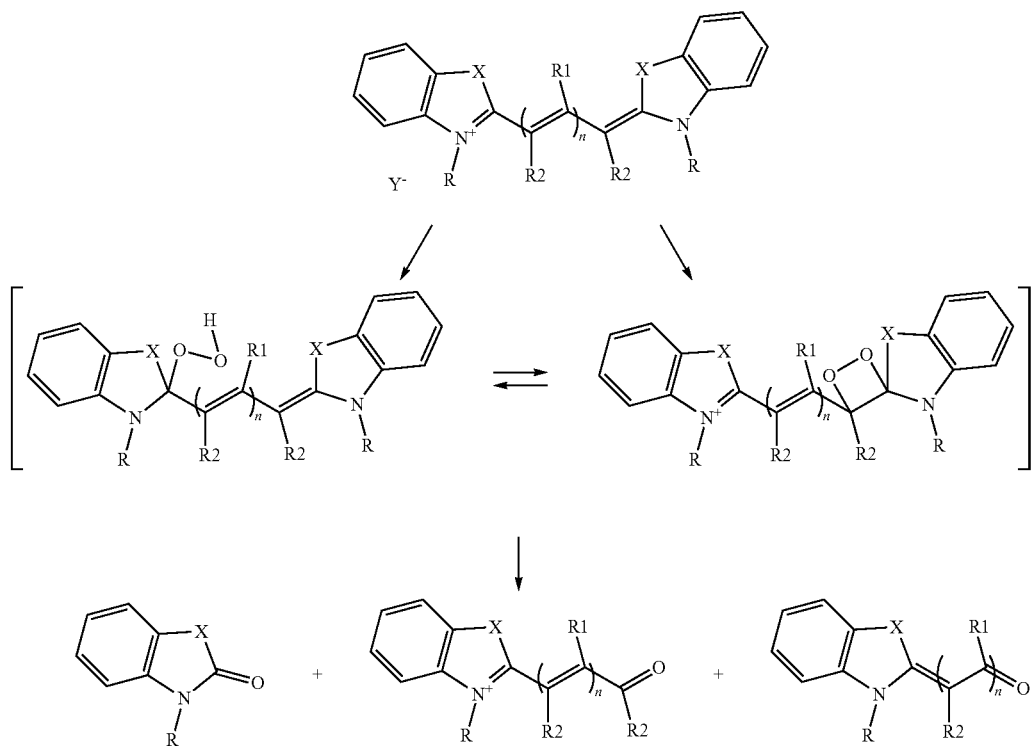

It has been postulated that the photo-bleaching ratio depends on Red-Ox potentials of dyes and correlate with availability of carbon atoms (especially those next to nitrogen atom) in a conjugation polymethine chain for interactions with active species. Thus, cyanine dyes of the invention, due at least in part to the N-aryl groups not only benefit from decreased aggregation but improved photochemical stability as well.

In some embodiments, compounds of Formula 2 can be used as starting materials for dye synthesis.

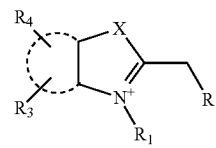

2

Wherein: Z are -, or an appropriate organic or inorganic counterion; X are —O—, —S—, —$CR_7R_8$; the dotted curve represents the non-metal (carbon or hetero-) atoms required to form one to three a benzo-, naphtho- or heterocyclic condensed rings having 5 to 7 atoms in each ring; $R_3$ and $R_4$ groups are attached to the rings;

R is hydrogen atom, halogen atom, alkyl group, alkoxy group, unsubstituted or substituted amino group, carboxy-, sulfo-, alkylsulfono- or arylsulfono-, sulfonato-, unsubstituted or substituted sulfonamido-, hydroxy-, unsubstituted or substituted (preferably substituted with hydrophilic or functional groups) alkyl/aryl groups;

$R_3$, $R_4$, each independently is hydrogen atom, halogen atom, alkyl group, alkoxy group, unsubstituted or substituted amino group, carboxy-, sulfo-, alkylsulfono- or arylsulfono-, sulfonato-, unsubstituted or substituted sulfonamido-, hydroxy-, unsubstituted or substituted (preferably substituted with hydrophilic or functional groups) alkyl/aryl groups;

$R_7$ and $R_8$ each independently represents alkyl, aryl or substituted alkyl, aryl groups (preferably substituted with hydrophilic or functional groups alike sulfo-, sulfonato, sulfonamido-, carboxy-, hydroxy-, amino-alkyl/aryl groups) or they can form a part of cyclic, or heterocyclic groups; characterized in that at least one of $R_3$ and $R_4$ groups is an amino-, substituted amino-carboxy-, carboxamido-, sulfo-, unsubstituted or substituted sulfonamido-, sulfonato-, alkylsulfono- or arylsulfono-, group or alkyl/aryl groups having substituents mentioned above; $R_1$ represents unsubstituted or substituted aryl or heteroaryl groups preferably substituted with hydrophilic groups like sulfo- or sulfonato-groups.

Reagents of Formula 2 can be used in the preparation of dyes of the present invention such as those shown below:

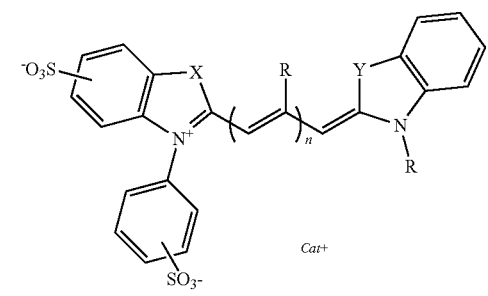

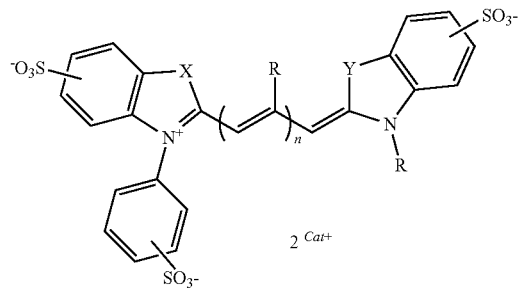

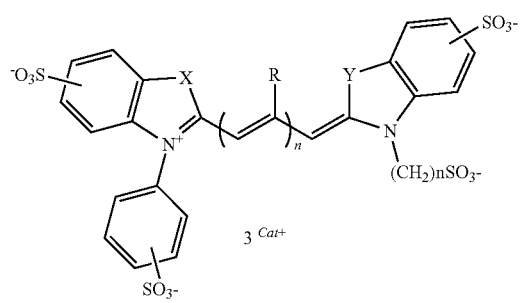

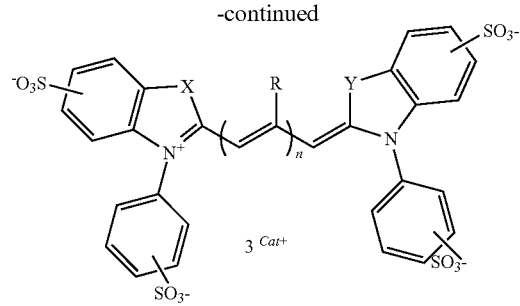

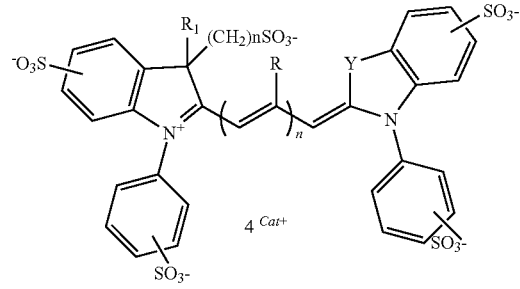

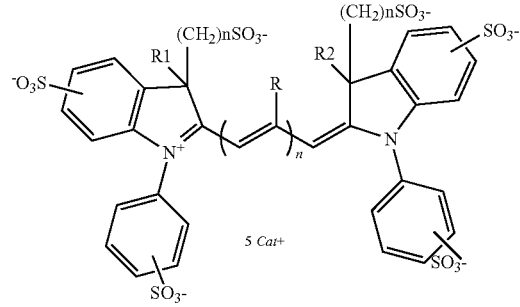

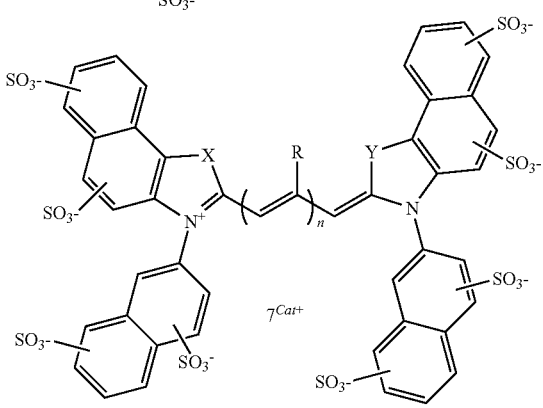

and also for preparation of another type of cyanine dyes such as the following:

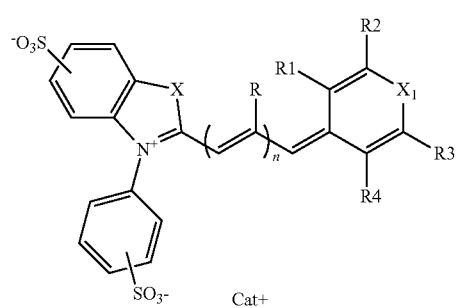

-continued

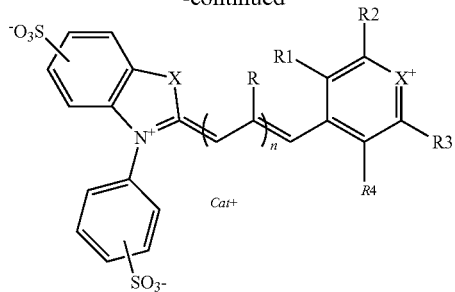

as well as for the preparation of other different classes of polymethine dyes like styryl and merocyanine dyes:

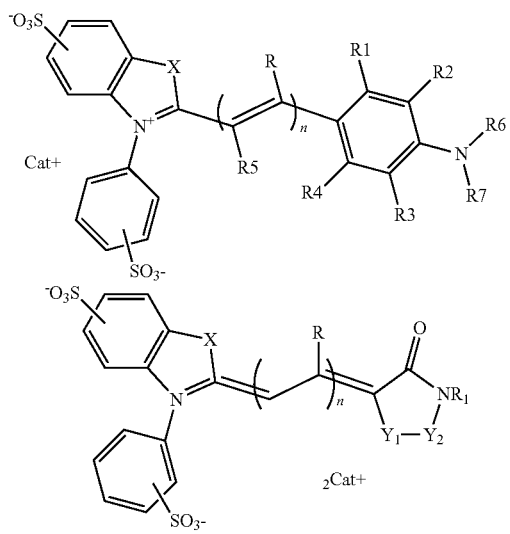

Without being bound by theory, such dyes may have not only higher photo-stability and strong fluorescence and possess larger Stocks shift of maximum of fluorescence band. Stocks shift is a parameter for fluorescent labels and represents a distance between absorption and fluorescence maximums.

For the synthesis of dyes of the invention, the reaction of $SO_3$ or its complexes or their solutions in organic or inorganic solvents with substrates like quaternary heterocyclic salts formula (3.1) or appropriate methylene bases was applied.

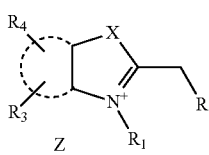
(3.1)

Wherein: Z are -, or an appropriate organic or inorganic counterion; X are —O—, —S—, —$CR_7R_8$; the dotted curve represents the non-metal (carbon or hetero-) atoms required to form one to three a benzo-, naphtho- or heterocyclic condensed rings having 5 to 7 atoms in each ring; $R_3$ and $R_4$ groups are attached to the rings;

$R_1$ represents unsubstituted or substituted aryl or heteroaryl groups

For example, starting from quaternary heterocyclic salts formula 3.2

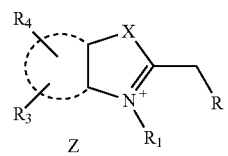
3.2

Wherein: Z are -, or an appropriate organic or inorganic counterion; X and Y are independently selected from the group consisting of —O—, —S—, —$CR_7R_8$, each dotted curve independently represent the non-metal (carbon or hetero-) atoms required to form one to three a benzo-, naphtho- or heterocyclic condensed rings having 5 to 7 atoms in each ring; $R_3$, $R_4$, $R_5$ and $R_6$ groups are attached to the rings;

$R_1$, $R_7$ and $R_8$ each independently represents alkyl, aryl, heteroaryl or substituted alkyl, aryl, heteroaryl groups (preferably substituted with hydrophilic or functional groups alike, sulfonamido-, carboxy-, hydroxy-, amino-alkyl/aryl groups) or they can form a part of cyclic, or heterocyclic groups; $R_3$, $R_4$, each independently is hydrogen atom, halogen atom, alkyl group, alkoxy group, amino group, carboxy-, sulfono-, sulfonamido-, hydroxy-, unsubstituted or substituted (preferably substituted with hydrophilic or functional groups) alkyl/aryl groups.

In some embodiments, the present invention provides a method of preparing organic compounds (heterocyclic derivatives) having the formula (I-2) by interaction of $SO_3$ or its complexes or their solutions in organic or inorganic solvents

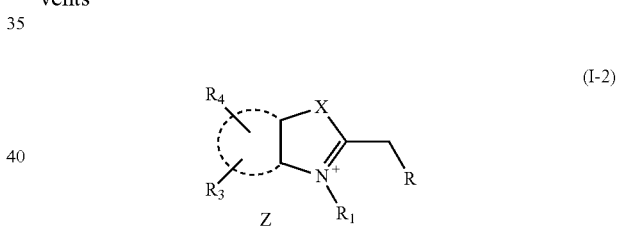
(I-2)

with substrates like quaternary heterocyclic salts formula (3.1, 3.2)

The term "alkoxy," as used herein refers to an alkyl ether group, wherein the term alkyl is as defined below. Examples of suitable alkyl ether groups include methoxy, ethoxy, n-propoxy, iso-propoxy, n-butoxy, iso-butoxy, sec-butoxy, tert-butoxy, and the like.

The term "alkyl," as used herein refers to a straight-chain or branched-chain alkyl group containing from 1 to 20 carbon atoms. In certain embodiments, the alkyl group will comprise from 1 to 12 carbon atoms. In further embodiments, the alkyl group will comprise from 1 to 6 carbon atoms, which can optionally be used interchangeably with the term "lower alkyl" group. In yet further embodiments, the alkyl group will comprise from 1 to 4 carbon atoms, which can also be used interchangeably with the term "lower alkyl" group. Alkyl groups can be optionally substituted as defined herein. Examples of alkyl groups include methyl, ethyl, n-propyl, iso-propyl, n-butyl, iso-butyl, sec-butyl, tert-butyl, pentyl, iso-amyl, hexyl, heptyl, octyl, nonyl, decyl, undecyl, dodecyl and the like. The term "alkylene" as used herein refers to a saturated aliphatic group derived from a straight or branched chain saturated hydrocarbon attached at two or more positions, such as methylene (—$CH_2$—). Unless otherwise specified, the term "alkyl" can include "alkylene" groups.

The term "aryl," as used herein means a carbocyclic aromatic system containing one, two or three rings wherein such polycyclic ring systems are fused together. The term "aryl" include, without limitation, aromatic groups such as phenyl, naphthyl, anthracenyl, and phenanthryl.

The term "aralkyl" or "arylalkyl," as used herein refers to an aryl group, as defined herein, attached to the parent molecular moiety through an alkyl group, as defined herein. An exemplary aralkyl is the benzyl group. Other aralkyl groups include, without limitation, phenylethyl, phenylpropyl, phenylbutyl, naphthylmethyl, naphthylethyl, napthylpropyl, anthracenylmethyl, anthracenylethyl, phenanthrylmethyl, and phenanthrylethyl.

The term "aralkoxy" or "arylalkoxy," as used herein refers to an aryl group, as defined herein, attached to the parent molecular moiety through an alkoxy group, as defined herein.

The term "alkene" or radical fragment "alkenyl," as used herein refers to a straight-chain or branched-chain hydrocarbon group having one or more double bonds and containing from 2 to 20 carbon atoms. In some embodiments, an alkene will comprise from 2 to 6 carbon atoms. The term "alkenylene" refers to a carbon-carbon double bond system attached at two or more positions such as ethenylene [(—CH=CH—),(—C::C—)]. Examples of suitable alkenyl groups include ethenyl, propenyl, 2-methylpropenyl, 1,4-butadienyl and the like. The term "alkenyl" can include "alkenylene" groups.

The term "alkenyloxy," as used herein refers to an alkenyl ether group, wherein the term alkenyl is defined herein. Examples of suitable alkenyl ether groups include allyloxy (2-propenoxy), vinyloxy (ethenoxy), 1-propenoxy, n-butenoxy, and the like.

The term "alkyne" or radical fragment "alkynyl," as used herein refers to a straight-chain or branched chain hydrocarbon group having one or more triple bonds and containing from 2 to 20 carbon atoms. In certain embodiments, the alkynyl group comprises from 2 to 6 carbon atoms. In further embodiments, the alkynyl group comprises from 2 to 4 carbon atoms. The term "alkynylene" refers to a carbon-carbon triple bond attached at two positions, such as ethynylene (—C:::C—, —C≡C—). Examples of alkynyl groups include ethynyl, propynyl, hydroxypropynyl, butyn-1-yl, butyn-2-yl, pentyn-1-yl, 3-methylbutyn-1-yl, hexyn-2-yl, and the like. The term alkynyl can include alkynylene groups.

The term "alkynyloxy" refers to an alkynyl ether group. Examples of suitable alkynyl ether groups include, ethynyloxy, 1-propynyloxy, propargyloxy (2-propynyloxy), butynyloxy, and the like.

The term "hydroxyalkyl" refers to an alkyl group bearing a hydroxyl moiety (—OH) on at least one carbon atom of the alkyl chain.

The term "halo" or "halogen" refers to fluorine, chlorine, bromine, or iodine.

The term "bond," as used herein refers to a covalent bond between two atoms and can include single, double, and triple bonds.

The term "optionally substituted" means the anteceding group can be substituted or unsubstituted. When substituted, the substituents of an "optionally substituted" group can include any of the substituents defined herein including, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents can be joined together to form a fused five-, six-, or seven-membered carbocyclic or heterocyclic ring consisting of zero to three heteroatoms, for example forming methylenedioxy or ethylenedioxy. An optionally substituted group can be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety can be defined as needed; in these cases, the optional substitution will be as defined, often immediately following the phrase, "optionally substituted with." The following substituent definitions are provided, which are within the scope of substituents embraced by the term optionally substituted, in addition to those substituents already defined above.

As used herein the term "lower alkyl ester" refers to a $C_1$-$C_6$ alkyl chain ester of a carboxylic acid. In some embodiments, a "lower alkyl ester" refers to a $C_1$-$C_4$ alkyl chain ester of a carboxylic acid. Representative esters include methyl, ethyl, propyl, butyl, pentyl, and hexyl esters. Any of the forgoing esters can be optionally branched. Such branched esters include iso-propyl esters, sec-butyl esters, iso-butyl esters and tert-butyl esters, for example.

The term "alkylamino," as used herein refers to an alkyl group attached to the parent molecular moiety through an amino group. Suitable alkylamino groups can be mono- or dialkylated, forming groups such as, for example, N-methylamino, N-ethylamino, N,N-dimethylamino, N,N-ethylmethylamino and the like.

The term "alkylidene," as used herein refers to an alkenyl group in which one carbon atom of the carbon-carbon double bond belongs to the moiety to which the alkenyl group is attached.

The term "alkylthio," as used herein refers to an alkyl thioether (R—S—) group wherein the term alkyl is as defined above and wherein the sulfur can be singly or doubly oxidized. Examples of suitable alkyl thioether groups include methylthio, ethylthio, n-propylthio, isopropylthio, n-butylthio, iso-butylthio, sec-butylthio, tert-butylthio, methanesulfonyl, ethanesulfinyl, and the like.

The terms "amido" and "carbamoyl," as used herein refer to an amino group as described below attached to the parent molecular moiety through a carbonyl group, or vice versa. The term "C-amido" as used herein refers to a —C(=O)—NR2 group with R as defined herein. The term "N-amido" as used herein refers to a RC(=O)NH— group, with R as defined herein. The term "acylamino" as used herein embraces an acyl group attached to the parent moiety through an amino group. An example of an "acylamino" group is acetylamino ($CH_3C(O)NH$—).

The term "amino," as used herein refers to —NRR', wherein R and R' are independently selected from the group consisting of hydrogen, alkyl, acyl, heteroalkyl, aryl, cycloalkyl, heteroaryl, and heterocycloalkyl, any of which can themselves be optionally substituted. Additionally, R and R' can combine to form heterocycloalkyl, either of which can be optionally substituted.

The term "arylalkenyl" or "aralkenyl" as used herein refers to an aryl group attached to the parent molecular moiety through an alkenyl group.

The term "arylalkynyl" or "aralkynyl" as used herein refers to an aryl group attached to the parent molecular moiety through an alkynyl group.

The term "arylalkanoyl" or "aralkanoyl" or "aroyl" as used herein refers to an acyl group derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein refers to an aryl group attached to the parent molecular moiety through an oxy.

The terms "benzo" and "benz" as used herein refer to the divalent group C6H4=derived from benzene. Examples include benzothiophene and benzimidazole.

The term "carbamate" as used herein refers to an ester of carbamic acid (—NHCOO—) which can be attached to the parent molecular moiety from either the nitrogen or acid end, and which can be optionally substituted as defined herein.

The term "O-carbamyl" as used herein refers to a —OC(O)NRR' group, with R and R' as defined herein.

The term "N-carbamyl" as used herein refers to a ROC(O)NR'— group, with R and R' as defined herein.

The term "carbonyl" as used herein, when alone includes formyl [—C(O)H] and in combination is a —C(O)— group.

The term "carboxyl" or "carboxy" as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano" as used herein refers to —CN.

The term "cycloalkyl" or "carbocycle" as used herein refers to a saturated or partially saturated monocyclic, bicyclic or tricyclic alkyl group wherein each cyclic moiety contains from 3 to 12 carbon atom ring members and which can optionally be a benzo fused ring system which is optionally substituted as defined herein. In certain embodiments, the cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by bicyclo[1,1,1]pentane, camphor, adamantane, and bicyclo[3,2,1]octane.

The term "ester," as used herein refers to a carboxy group bridging two moieties linked at carbon atoms.

The term "ether," as used herein refers to an oxy group bridging two moieties linked at carbon atoms.

The term "haloalkoxy," as used herein refers to a haloalkyl group attached to the parent molecular moiety through an oxygen atom.

The term "haloalkyl," as used herein refers to an alkyl group having the meaning as defined above wherein one or more hydrogens are replaced with a halogen. Specifically embraced are monohaloalkyl, dihaloalkyl and polyhaloalkyl groups. A monohaloalkyl group, for one example, can have an iodo, bromo, chloro or fluoro atom within the group. Dihalo and polyhaloalkyl groups can have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein refers to a stable straight or branched chain, or cyclic hydrocarbon group, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms can optionally be oxidized and the nitrogen heteroatom can optionally be quaternized. The heteroatom(s) O, N and S can be placed at any interior position of the heteroalkyl group. Up to two heteroatoms can be consecutive, such as, for example, —CH$_2$—NH—OCH$_3$.

The term "heteroaryl," as used herein refers to a 3 to 7 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, the heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein each refer to a saturated, partially unsaturated, or fully unsaturated monocyclic, bicyclic, or tricyclic heterocyclic group containing at least one heteroatom as a ring member, wherein each the heteroatom can be independently selected from the group consisting of nitrogen, oxygen, and sulfur. In certain embodiments, the heterocycloalkyl will comprise from 1 to 4 heteroatoms as ring members. In further embodiments, the heterocycloalkyl will comprise from 1 to 2 heteroatoms as ring members. In certain embodiments, the heterocycloalkyl will comprise from 3 to 8 ring members in each ring. In further embodiments, the heterocycloalkyl will comprise from 3 to 7 ring members in each ring. In yet further embodiments, the heterocycloalkyl can comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups can be optionally substituted unless specifically prohibited.

The term "hydrazinyl" as used herein refers to two amino groups joined by a single bond, i.e., —N—N—.

The term "hydroxy," as used herein refers to —OH.

The term "hydroxyalkyl," as used herein refers to a hydroxy group attached to the parent molecular moiety through an alkyl group.

The term "imine" or "imino," as used herein refers to RN=.

The term "iminohydroxy," as used herein refers to N(OH)C— and N—O—.

The term "isocyanato" refers to a —NCO group.

The term "isothiocyanato" refers to a —NCS group.

The term "lower," as used herein, alone or in a combination, where not otherwise specifically defined, means containing from 1 to 6 carbon atoms, inclusive. In some embodiments, lower means containing from 1 to 4 carbon atoms, inclusive.

The term "lower aryl," as used herein means phenyl or naphthyl, which can be optionally substituted as provided.

The term "lower heteroalkyl," as used herein refers to a stable straight or branched chain, or cyclic hydrocarbon group, or combinations thereof, fully saturated or containing from 1 to 3 degrees of unsaturation, consisting of one to six atoms in which one to three can be heteroatoms selected from the group consisting of O, N, and S, and the remaining atoms are carbon. The nitrogen and sulfur atoms can optionally be oxidized and the nitrogen heteroatom can optionally be quaternized. The heteroatom(s) O, N and S can be placed at any interior or terminal position of the heteroalkyl group. Up to two heteroatoms can be consecutive, such as, for example, —CH$_2$—NH—OCH$_3$.

The term "lower heteroaryl," as used herein means either 1) monocyclic heteroaryl comprising five or six ring members, of which between one and four of the members can be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein means a monocyclic cycloalkyl having between three and six ring members. Lower cycloalkyls can be unsaturated. Examples of lower cycloalkyl include cyclopropyl, cyclobutyl, cyclopentyl, and cyclohexyl.

The term "lower heterocycloalkyl," as used herein means a monocyclic heterocycloalkyl having between three and six ring members, of which between one and four can be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls can be unsaturated.

The term "lower amino," as used herein refers to —NRR', wherein R and R' are independently selected from the group consisting of hydrogen, lower alkyl, and lower heteroalkyl, any of which can be optionally substituted. Additionally, the R and R' of a lower amino group can combine to form a five—or six—membered heterocycloalkyl, either of which can be optionally substituted.

The term "mercaptyl" as used herein refers to an RS— group, where R is as defined herein.

The term "nitro," as used herein refers to —NO$_2$.

The terms "oxy" or "oxa," as used herein refer to —O—.

The term "oxo," as used herein refers to =O.

The term "perhaloalkoxy" refers to an alkoxy group where all of the hydrogen atoms are replaced by halogen atoms.

The term "perhaloalkyl" as used herein refers to an alkyl group where all of the hydrogen atoms are replaced by halogen atoms.

The terms "sulfonate," "sulfonic acid," and "sulfonic," as used herein refer to the —SO$_3$H group and its anion as the sulfonic acid is used in salt formation.

The term "sulfanyl," as used herein refers to —S—.

The term "sulfinyl," as used herein refers to —S(O)—.

The term "sulfonyl," as used herein refers to —S(O)$_2$—.

The term "N-sulfonamido" refers to a RS(=O)$_2$NR'— group with R and R' as defined herein.

The term "S-sulfonamido" refers to a —S(=O)2NRR', group, with R and R' as defined herein.

The terms "thia" and "thio," as used herein refer to a —S— group or an ether wherein the oxygen is replaced with sulfur. The oxidized derivatives of the thio group, namely sulfinyl and sulfonyl, are included in the definition of thia and thio.

The term "thiol," as used herein refers to an —SH group.

The term "thiocarbonyl," as used herein, when alone includes thioformyl —C(S)H and in combination is a —C(S)— group.

The term "N-thiocarbamyl" refers to an ROC(S)NR' group, with R and R' as defined herein.

The term "O-thiocarbamyl" refers to a —OC(S)NRR' group with R and R' as defined herein.

The term "thiocyanato" refers to a —CNS group.

Any definition herein can be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

In some embodiments, the present invention provides a compound of Formula I or its mesomer as shown below:

wherein

CI is a charge balancing counterion and p is an integer from 1-7;

m is 1, 3, 5, 7, or 9;

each incidence of X is independently hydrogen, halogen, alkyl- or aryloxy, alkyl- or arylthio, amino- or substituted amino, aryl, or alkyl, any of which may be optionally substituted with a substituent selected from carboxyl, sulfonate, sulfinate, sulfoxide, sulfone, sulfonamide, hydroxyl, amino, alkylamino, dialkylamino, alkoxy, and halogen; optionally, one or more X groups are combined to form a carbocyclic ring;

Y is independently selected from O, $NR_a$, S, Se, $CR_b$=CR, and $CR_2R_3$;

Z is independently selected from O, $NR_a$, S, Se, $CR_b$=CR, and $CR_4R_5$; Wherein $R_{a,b,c}$, $R_2$, $R_3$, $R_4$, and $R_5$ are independently selected from alkyl, aryl or substituted alkyl like aminoalyl, carboxyalkyl, sulfoalkyl; substituted aryl like carboxyaryl, sulfoaryl $R_1$ is selected from aryl (for example phenyl, naphthyl) or alkyl, any of which may be optionally substituted with at least one substituent selected from carboxyl, sulfonate, sulfinate, sulfoxide, sulfone, sulfonamide, hydroxyl, amino, alkylamino, dialkylamino, alkoxy, halogen, succinimidyl ester, ester, and amide;

$R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ are independently selected from carboxyl, sulfonate, sulfinate, sulfoxide, sulfone, sulfonamide, hydroxyl, amino, alkylamino, dialkylamino, alkoxy, halogen, alkyl succinimidyl ester, ester, amide, or any ortho-disposed pair of $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ is combined to form a further fused aromatic or heterocyclic ring which is optionally substituted; wherein at least one of $R_{14}$, $R_{15}$, $R_{16}$, $R_{17}$, or $R_{18}$ is sulfonate or a further fused aromatic ring derived from $R_{14}$, $R_{15}$, $R_{16}$, $R_{17}$, or $R_{18}$ comprises at least one sulfonate substituent; with the proviso that none of $R_{14}$, $R_{15}$, $R_{16}$, $R_{17}$, and $R_{18}$ are carboxyl.

In some embodiments, the present invention provides compounds of the structure IA or mesomer thereof:

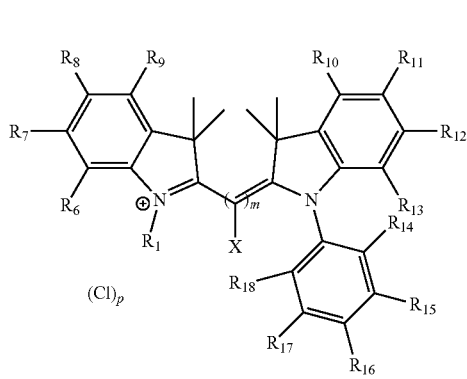

IA

In some embodiments, the present invention provides compounds of the structure IB or mesomer thereof:

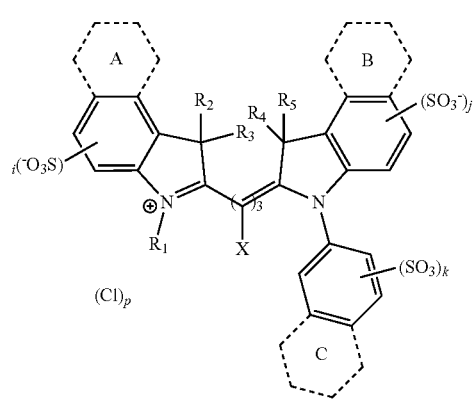

IB wherein i and j are, independently, 0, 1, or 2; k is 1 or 2; and A, B, and C are independently, optional further ring fusion.

In some embodiments, dyes of the present invention provides compounds of the structure IC or mesomer thereof:

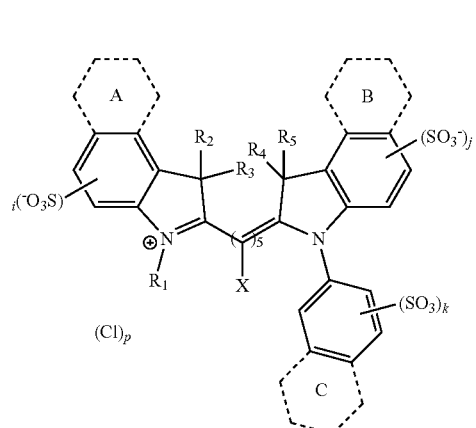

IC wherein i and j are, independently, 0, 1, or 2; k is 1 or 2; and A, B, and C are independently, optional further ring fusion.

In some embodiments, the present invention provides compounds having the structure ID or mesomer thereof:

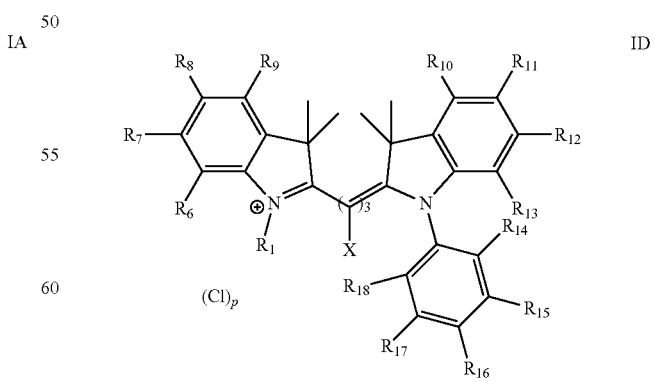

ID

In some embodiments, compounds of the present invention have the structure ID1 or mesomers thereof:

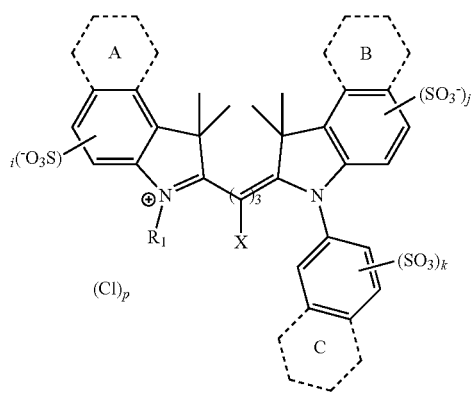

ID1 wherein i and j are, independently, 0, 1, or 2; k is 1 or 2; and A, B, and C are independently, optional further benzene ring fusion.

In some embodiments, the present invention provides compounds of the structure IE or mesomer thereof:

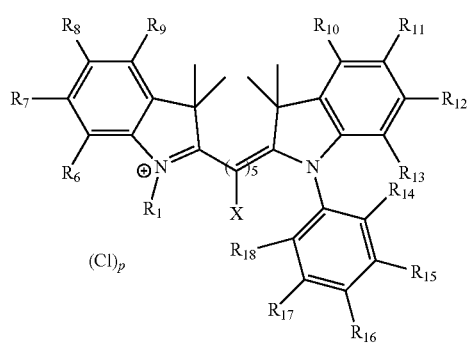

IE

In some embodiments, the present invention provides compounds having the structure IE1 or mesomer thereof.

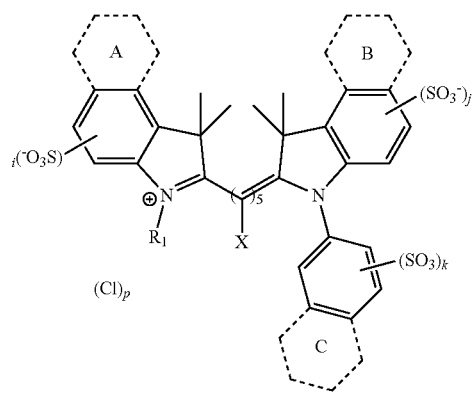

IE1 wherein i and j are, independently, 0, 1, or 2; k is 1 or 2; and A, B, and C are independently, optional further ring fusion.

In some embodiments, compounds of the present invention are selected from:

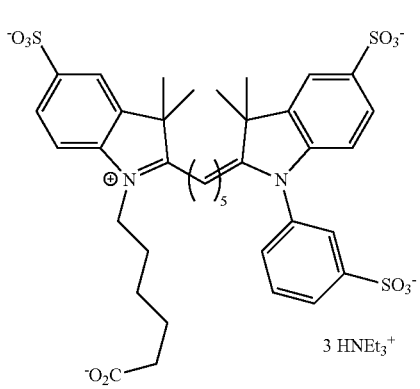

(i)

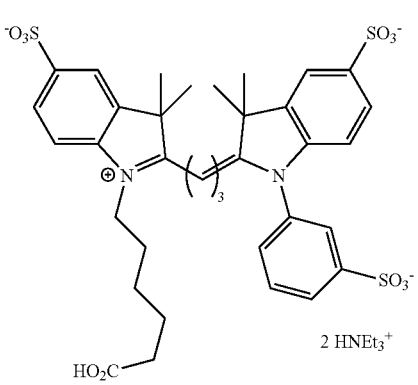

(ii)

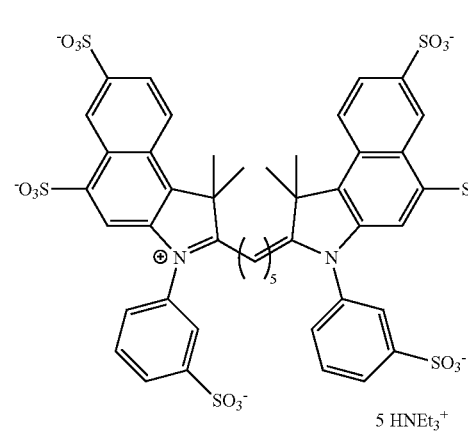

(iii)

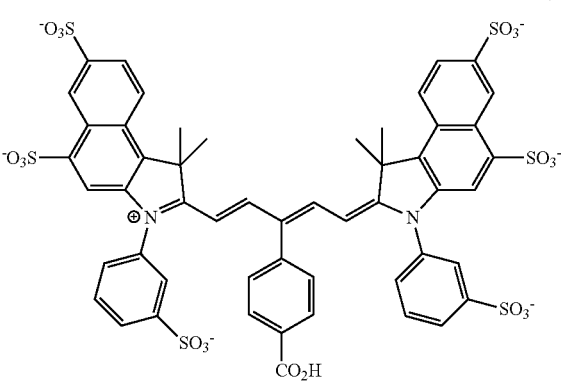

(iv)

-continued (v)
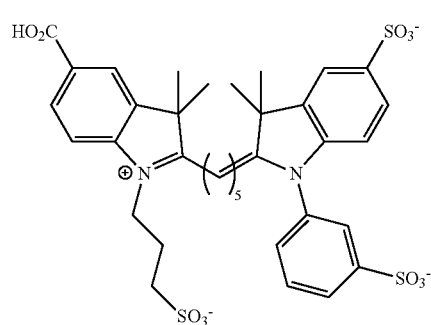
2 HNEt$_3^+$ (vi)
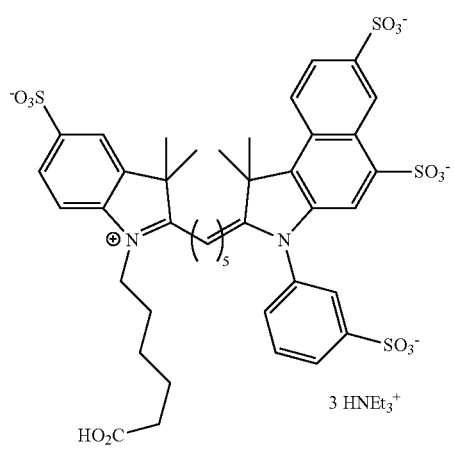
3 HNEt$_3^+$ (vii)
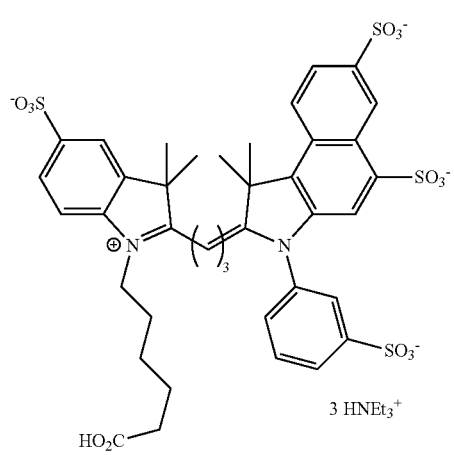
3 HNEt$_3^+$ In some embodiments, the present invention provides a method of making a compound of formula I, as described above, the method including condensing a compound comprising formula IIA or IIB:

IIA
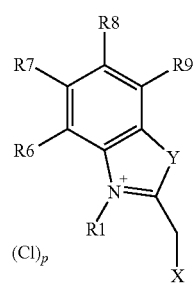

IIB
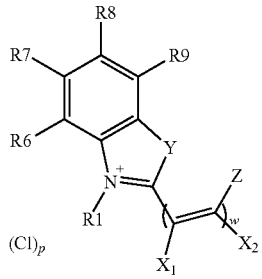

Wherein Z=OR, SR, NHR or NR; w=0, 1, 2, 3 with a compound comprising formula IIIA or IIIB respectively:

III

IIIA
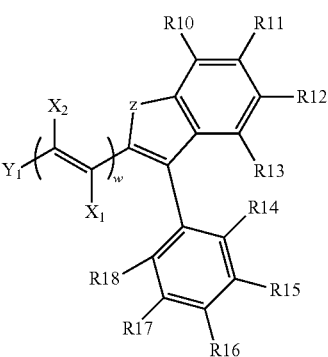

IIIB
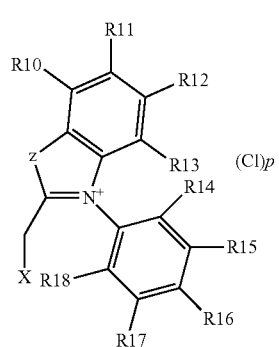

wherein Y1 is NHR, NR$_d$R$_e$, XR$_o$, (where X=O, S); w is 0, 1, 2 or 3 In some embodiments, the present invention provides dyes having structure 1-P or mesomer thereof:

1-P
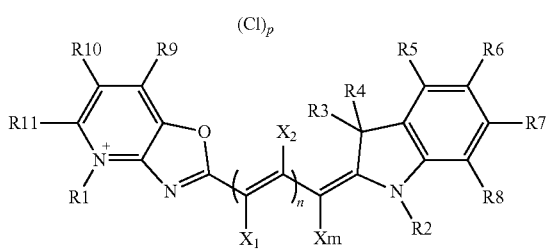

wherein m=2n+1; n=0, 1, 2, 3 but to attain maximum absorption at 532 nm preferably: n=1; $X_1$-$X_m$=H or alkyl or substituted alkyl; aryl or substituted aryl; arylalkyl or Heteroarylalkyl; which together or with R may form a cyclic or heterocyclic ring; heteroatom or alkyl(aryl)substituted heteroatom; $R^1$, $R^2$, $R^3$, $R^4$=H, Alkyl or substituted alkyl; Aryl or substituted aryl; Arylalkyl or Heteroarylalkyl; $R^5$-$R^{11}$=H; Alkyl or substituted alkyl; Aryl or substituted aryl; Arylalkyl or Heteroarylalkyl; any of $R^1$-$R^{11}$ maybe or may contain functional groups such as $SO_3$, $SO_3H$, $SO_2NR_{12}R_{13}$, COO, COOH, $COOR_{14}$, $CONR_{15}R_{16}$; halide, Amino or substituted amino, nitro, carbonyl, azido; and one of $R^1$-$R^{16}$ substituents or combinations thereof can contain saturated and/or unsaturated Carbon-Carbon or Carbon-Heteroatom single, double or triple bonds such as two, three or more neighboring groups from $R^5$-$R^{11}$ may form a cyclic/heterocyclic ring(rings)

$R^1$-$R^{16}$=$(CH2)_LCCH$; $(CH2)_LN3$; $(CH2)_LCN$ where L=1-5

Dyes of structure 1-P can be prepared from heterocyclic derivatives 2-P, 3-P using both known and new compounds as starting materials by reaction with intermediates commonly used in cyanine dyes chemistry:

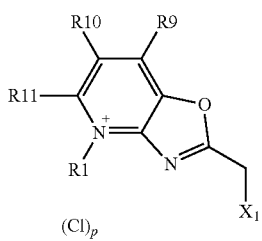

2-P

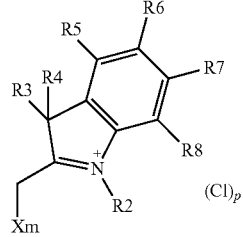

3-P

Some 2-methyloxazolo[4,5-b]pyridinium derivatives (Dyes & Pigments 2005 v 66 pp 135-142; Dyes & Pigments 2007 v 75 pp 466-473) and substituted 2,3,3-trimethyl-3H-indolium derivatives (3) (Waggoner, US(1993)5268486) were used previously for some other types dye synthesis.

To improve the yield of unsymmetrical dye structure 1-P, synthesis yield can be improved by performing a two-step reaction where hemicyanines 4-P or 5-P are produced first.

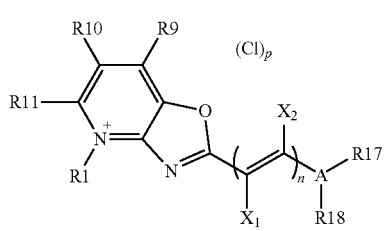

4-P

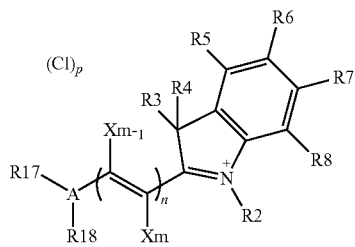

5-P wherein A=Heteroatom (N, O, S); $R^{17}$, $R^{18}$=-, H, Alkyl, Aryl or Heteroaryl, $COR^{19}$ It is understood that modifications which do not substantially affect the activity of the various embodiments of this invention are also provided within the definition of the invention provided herein. Accordingly, the following examples are intended to illustrate but not limit the present invention.

Example I 2,3,3-Trimethyl-1-(3-sulfophenyl)-3H-indolium-5-sulfonate

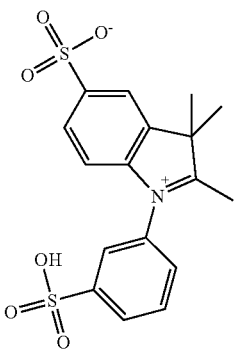

CP-1

This Example shows the preparation of coupling partner CP-1, an intermediate useful in the preparation of dyes of the present invention.

A mixture of 1 g (3 mmol) of 2,3,3-trimethyl-1-phenyl-3H-indolium hydrosulphate and 3 ml fuming sulphuric acid was heated five hours at 70° C. The product was precipitated with diethyl ether and washed with acetone and ethanol to provide 0.75 g (63%) of CP-1.

Example II 2,3,3-Trimethyl-1-phenyl-3H-indolium-5-sulfonate

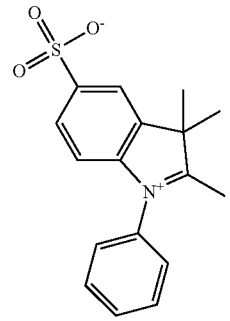

CP-2

This Example shows the preparation of coupling partner CP-2, an intermediate useful in the preparation of dyes of the present invention.

A mixture of 1 g (4.25 mmol) of 2-methylene-3,3-trimethyl-1-phenyl)-2,3-dihydro-1-H-indole and 1 ml fuming sulphuric acid was stirred at room temperature one hour then heated at 70° C. for three hours. The product was precipitated with diethyl ether and washed with acetone and ethanol to provide 0.7 g (52%) of CP-2.

Example III

3-Ethyl-2-methyl-benzothiazolium-6-sulfonate

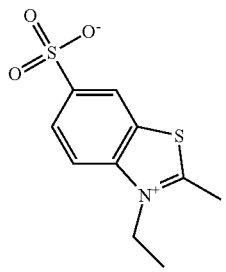

CP-3

This Example shows the preparation of coupling partner CP-3, an intermediate useful in the preparation of dyes of the present invention.

A mixture of 0.5 g (4.25 mmol) of 2-methyl-3-ethyl-benzothiazolium tosylate and 2 ml fuming sulphuric acid was stirred at room temperature for one hour then heated at 50° C. for three hours. The product was precipitated with diethyl ether and washed with acetone and ethanol to provide 0.35 g (95.3%) of CP-3.

Example IV 3-(3-Sulfopropyl)-2-methyl-5-methoxy-benzothiazolium-6-sulfonate

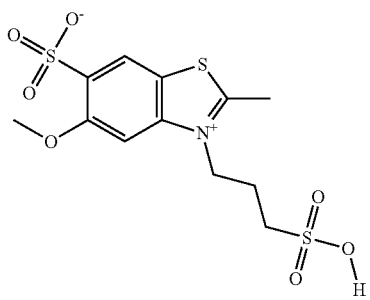

CP-4

This example shows the preparation of coupling partner CP-4, an intermediate useful in the preparation of dyes of the present invention.

A mixture of 0.3 g (1 mmol) of 2-methyl-5-metoxy-3-(3-sulfonatopropyl)benzothiazolium and 1 ml fuming sulphuric acid was stirred at room temperature for one hour then heated at 50° C. for three hours. The product was precipitated with diethyl ether and washed with acetone and ethanol to provide 0.25 g (66%) CP-4.

Example V 1-(3-Sulfopropyl)-2,3,3-trimethyl-3H-indolium-5-sulfonate

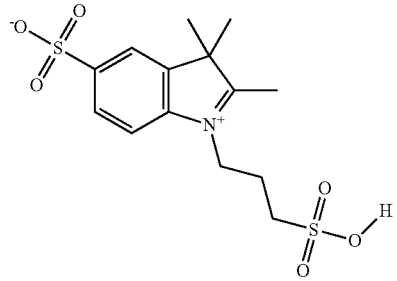

CP-5

This example shows the preparation of coupling partner CP-5, an intermediate useful in the preparation of dyes of the present invention.

A mixture of 0.5 g (1.8 mmol) of 1-(3-sulfonatopropyl)-2,3,3-trimethyl-3H-indolium and 2 ml fuming sulphuric acid was stirred at room temperature for one hour then heated at 40° C. for three hours. The product was precipitated with diethyl ether and washed with acetone and ethanol to provide 0.7 g (99%) of CP-5.

Example VI 3-(3-Sulfopropyl)-2-methyl-benzothiazolium-6-sulfonate

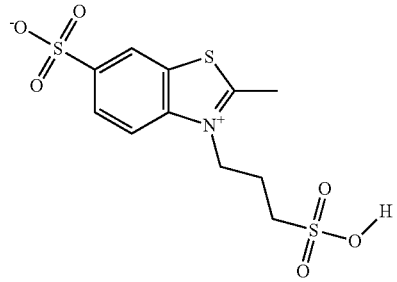

CP-6

This Example shows the preparation of coupling partner CP-6, an intermediate useful in the preparation of dyes of the present invention.

A mixture of 0.25 g (0.9 mmol) of 3-(3-sulfonatopropyl)-2-methyl-benzothiazolium and 2 ml fuming sulphuric acid was stirred at room temperature one hour then heated at 25° C. for 24 hours. The product was precipitated with diethyl ether and washed with acetone and ethanol to provide 0.1 g (30%) of CP-6.

Example VII

1-Ethyl-2,3,3-trimethyl-3H-indolium-5-sulfonate

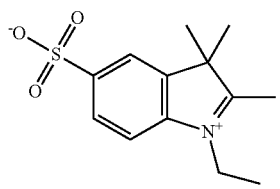

CP-7

This Example shows the preparation of coupling partner CP-7, an intermediate useful in the preparation of dyes of the present invention.

A mixture of 0.5 g (1.9 mmol) of 1-ethyl-2,3,3-trimethyl-3H-indolium tosylate and 2.5 ml fuming sulphuric acid was stirred at room temperature for 24 hours. The product was precipitated with diethyl ether and washed with acetone and ethanol to provide 0.35 g (68%) of CP-7.

Example VIII 1-(5-Carboxypenthyl)-2,3,3-trimethyl-3H-indolium-5-sulfonate

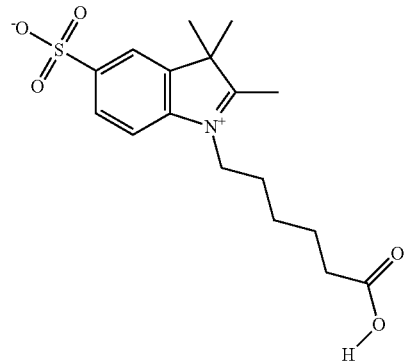

CP-8

This Example shows the preparation of coupling partner CP-8, an intermediate useful in the preparation of dyes of the present invention.

A mixture of 0.35 g (1 mmol) of 1-(carboxypenthyl)-2,3,3-trimethyl-3H-indolium bromide and 2 ml fuming sulphuric acid was stirred at room temperature for 24 hours. The product was precipitated with diethyl ether and washed with acetone and ethanol to provide 0.15 g (43%) of CP-8.

Example IX

3-Ethyl-1,1,2-trimethyl-7-sulfo-1H-benzo[e]indolium-5-sulfonate

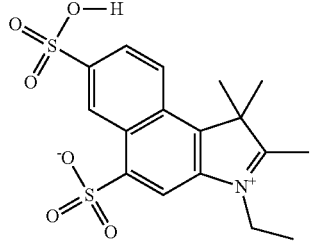

CP-9

This Example shows the preparation of coupling partner CP-9, an intermediate useful in the preparation of dyes of the present invention.

A mixture of 3.17 g (10 mmol) of 3-ethyl-1,1,2,-trimethyl-1H-benzo[e]indolium-7-sulphonate and 10 ml fuming sulphuric acid was stirred at 25° C. for 48 hours then heated at 70° C. for 5 hours. The product was precipitated with diethyl ether and washed with acetone and ethanol to provide 3.5 g (88%) of CP-9.

Although sulfonated benzo[e]indolium systems have been incorporated into cyanine dyes, such compounds, exemplified by betaine CP-9A and 6,8-disulfonated derivative CP-9B, are either only monosulfonated or possess two sulfonate groups on the same single ring.

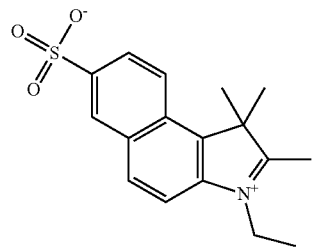

CP-9A

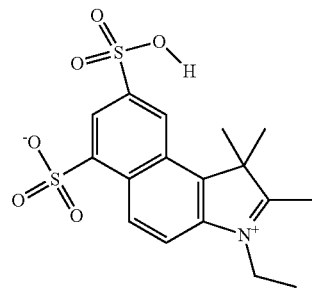

CP-9B

CP-9 and related dyes based on the 5,7-disulfonated benzoindolium skeleton can exhibit improved photostability, provide improved water solubility and can exhibit a diminished tendency to aggregate compared to cyanine dyes based on their counterparts CP-9A and CP-9B. Moreover, the generality of the synthetic procedure is amendable to the preparation of N-aryl-substituted analogues of quaternary benzoindolium derivatives such as CP-9C below:

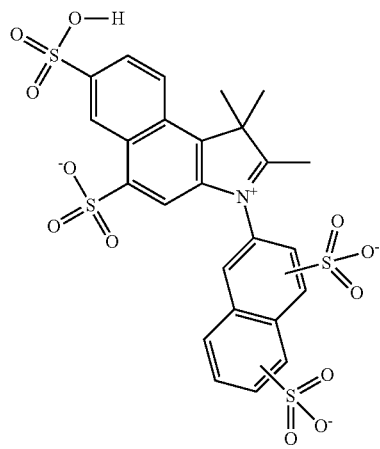

CP-9C

Example X

3-Ethyl-2-methyl-7-sulfo-naphtho[2,1-d]thiazolium-5-sulfonate

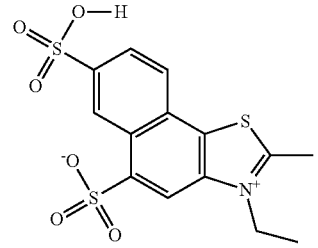

CP-10

This Example shows the preparation of coupling partner CP-10, an intermediate useful in the preparation of dyes of the present invention.

A mixture of 0.5 g (1.25 mmol) of 3-ethyl-2-methyl-naphtho[2,1-d]thiazolium tosylate and 5 ml fuming sulphuric acid was stirred at 70° C. for 5 hours. The product was precipitated with diethyl ether and washed with acetone and ethanol to provide 0.3 g (62%) of CP-10, which could be further purified by conventional column chromatography.

Example XI

3-Ethyl-2-methyl-benzoxazolium-5- and 3-ethyl-2-methyl-benzoxazolium-6-sulfonate

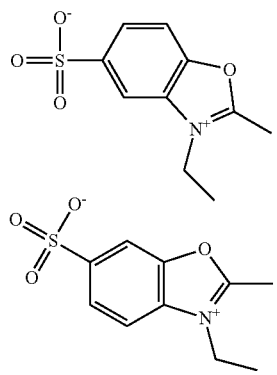

CP-11

CP-12

This Example shows the preparation of coupling partners CP-11 and CP12, intermediates useful in the preparation of dyes of the present invention.

A mixture of 0.33 g (1 mmol) of 2-methyl-3-ethyl-benzoxazolium tosylate and 2 ml fuming sulphuric acid was stirred at room temperature for one hour then heated at 50° C. for four hours. The product was precipitated with diethyl ether washed with acetone and ethanol to provide 0.1 g (41%) of a mixture of CP-11 and CP-12. The isomers are separated by crystallisation from methanol with isomer CP-12 as the main fraction CP-11 isolated from the filtrate.

It has been indicated that cyanine dyes based on the benzoxazolium structure exhibit strong fluorescence and can exhibit improved stability relative to indocarbo- and dicarbocyanine-based systems. Thus, dyes based on coupling partners CP-11 and CP-12, as well as N-arylated versions thereof, are expected to be strong fluorescent dye candidates.

Example XII

Dye 1

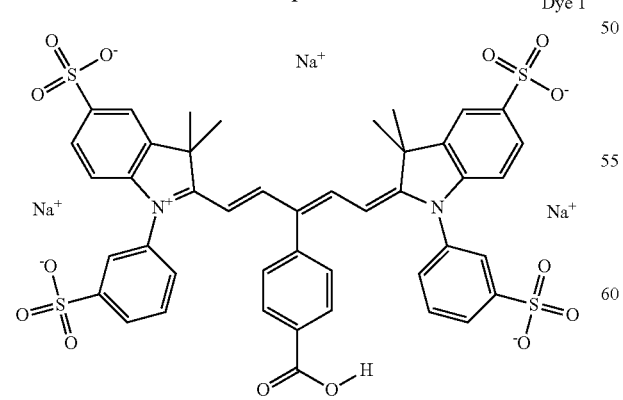

This Example shows the preparation of exemplary compound Dye 1 and comparison of its physical properties.

A mixture of 80 mg (0.2 mmol) of 2,3,3-trimethyl-1-(3-sulfophenyl)-3H-indolium-5-sulfonate (CP-1), 20 mg 2-(4-carboxyphenyl)malonicdialdehyde, 0.5 ml pyridine in 1 ml of acetic anhydride was heated for three minutes at 145° C. under microwave irradiation. The product was precipitated with diethyl ether and converted to its sodium salt. The product was purified by HPLC providing 0.02 g (25%) of Dye 1, which shows an absorption maximum at 658 nm in aqueous solution.

In a comparison of photo-stability of solutions of Dye 1 and Alexa 647 in water, dye 1 shows improved photostability relative to these commercial dyes. After 25 days of irradiation the solution of Dye 1 still possessed 85% of its initial fluorescence intensity.

Example XIII

Dye 2

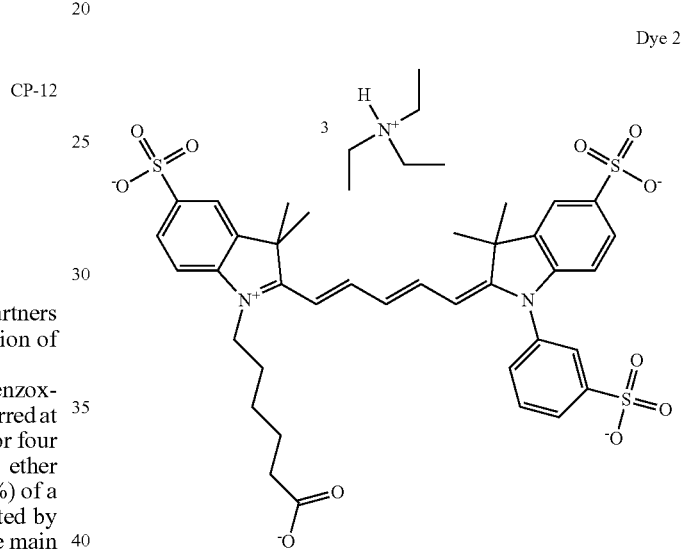

This Example shows the preparation of exemplary compound Dye 2 and its physical properties.

A mixture of 0.395 g (1 mmol) of 2,3,3-trimethyl-1-(3-sulfophenyl)-3H-indolium-5-sulfonate (CP-1, Example I) and 0.525 g (1 mmol) 2-(4-acetanilidobutadienyl)-3,3-dimethyl-1-(5-carboxypentyl)-3H-indolium-5-sulfonate:

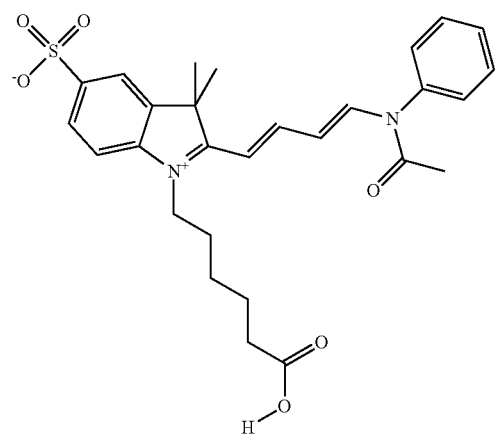

in 3 ml of acetic anhydride and 0.3 g triethylamine was heated for 20 minutes at 110° C. The acetic anhydride was removed under reduced pressure and the product precipitated with ethylacetate to provide 0.6 g (55%) of Dye 2, which could be further purified by HPLC.

Dye 2 exhibits an absorption maximum at 647 nm in water. Dye 2 stability was also compared against the stability of Cy5 (GE Healthcare) in water after six days storage of a solution on a bench top. Dye 2 maintained better fluorescence intensity over the six day test period. Dye 2 stability was also measured by absorbance decay, with a comparison to Cy5 and Alexa647 in water after irradiation by 660 nm laser. Dye 2 was more stable in water compared than the structurally similar commercial dyes Cy5 and Alexa647.

Example XIV

Dye 3

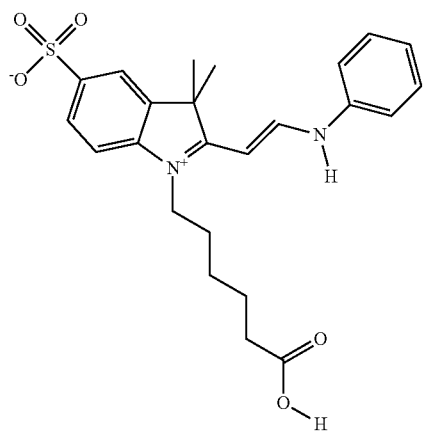

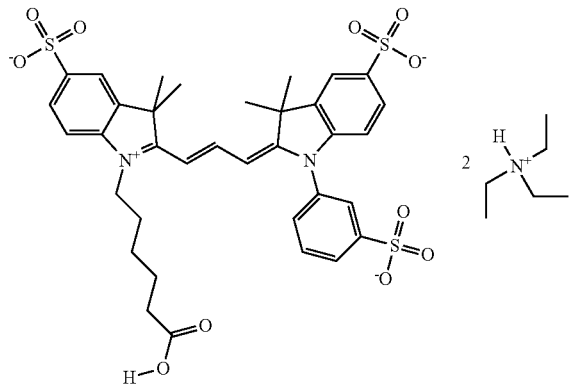

This Example shows the preparation of exemplary compound Dye 3 and its physical properties.

A mixture of 0.395 g (1 mmol) of 2,3,3-trimethyl-1-(3-sulfophenyl)-3H-indolium-5-sulfonate (CP-1, Example I), 0.457 g (1 mmol) 2-(2-anilinovinyl)-3,3-dimethyl-1-(5-carboxypentyl)-3H-indolium-5-sulfonate:

in 5 ml of acetic anhydride and 0.3 g triethylamine was heated for 20 minutes at 110° C. The acetic anhydride was removed under reduced pressure and the product precipitated with ethylacetate to provide 0.65 g (68%) Dye 3, which could be further purified by HPLC. Dye 3 exhibits an absorption maximum at 550 nm in water.

Figure 2:
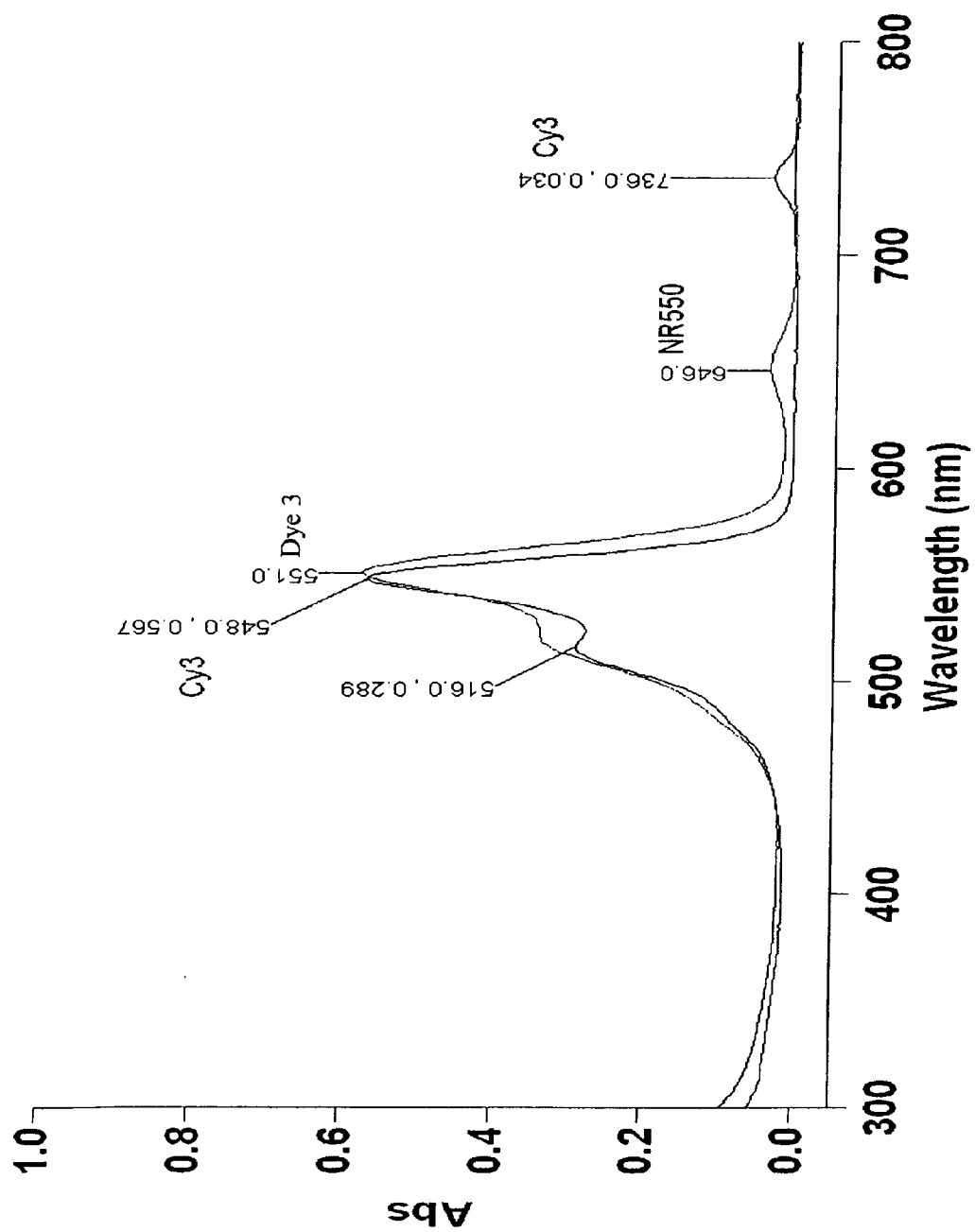
FIG. 2 shows an overlay of the absorption spectra of Dye 3 of the present invention with commercial dye Cy3.

The fluorescence intensity of Dye 3 (331 a.u. at 575 nm) compared with Cy3 (422 a.u. at 565 nm) in water at the same optical density of solution under excitation at 545 nm. FIG. 2 shows an overlay of the absorption spectrum of Dye 3 with Cy3 in water. As shown in FIG. 2, the fluorescence max for the Dye 3 Red shifted with a slightly larger Stokes shift (about 25 nm) and as a result provides better separation of the fluorescence signal from the excitation wavelength. Moreover, the integrated fluorescence intensity is higher for Dye 3 even at Cy3 absorption maximum. Dye 3 also exhibits better stability over time compared to Cy3, where after 14 days, the optical density of Cy3 is 85% compared to 94% with Dye 3.

Example XV

Dye 4

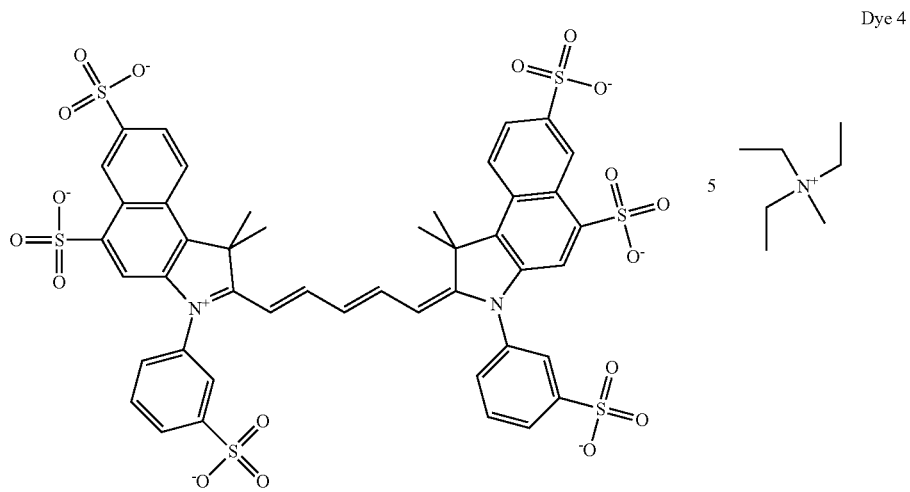

This Example shows the preparation of exemplary compound Dye 4 and its physical properties.

A mixture of 36 mg of 1,1,3-trimethyl-3-(3-sulfophenyl)-1H-benzo[e]indolium-disulfonate (CP-13B):

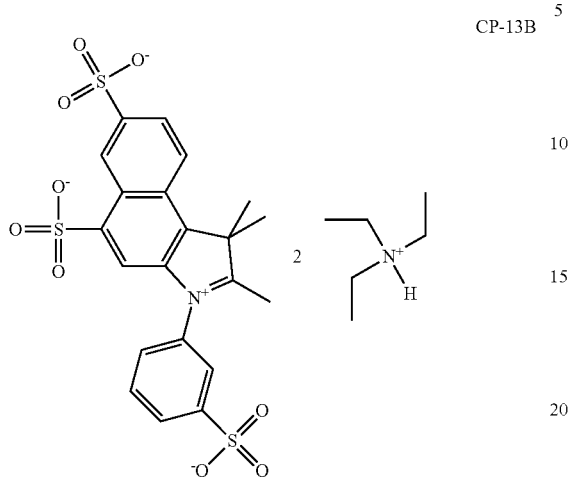

and 10 mg malonic aldehyde dianil hydrochloride, 0.5 mL acetic anhydride and 0.5 ml pyridine was heated at 120° C. for 5 minutes. The acetic anhydride removed under reduced pressure and the product precipitated with ethylacetate to provide 15 mg of Dye 4, which exhibited an absorption maximum at 683 nm in water.

Dye 4 exhibited similar absorption as commercially available dyes for the same spectral region: Dy681 and Dy682 (Dyomics GmbH, Jena, Germany). However, the fluorescence maximum for Dye 4 has bathochromic shift and as a result provides better separation of the fluorescent signal from excitation wavelength and less cross-talk with 660 dye. Dye 4 also had higher fluorescence intensity than Dy681 and Dy682.

Preparation of coupling partner 13B, 1,1,3-Trimethyl-3-(3-sulfophenyl)-1H-benzo[e]indolium-disulfonate triethylammonium salt:

1,1,2-Trimethyl-3-phenyl-1H-benzo[e]indolium perchlorate

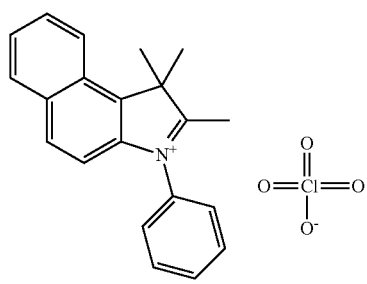 [SMILES: CC1=[N+](c2ccccc2)c2ccc3ccccc3c2C1(C)C ; [O-][Cl+3]([O-])([O-])[O-]]

N-Phenyl-N-(2-naphthyl)hydrazine (2.3 g) (or hydrochloride (2.7 g)) was dissolved in 50 ml of ethanol and 10 g of 3-methyl-butanone-2 was added. To this mixture 10 ml 70% perchloric acid was added slowly with stirring at room temperature. Stirring was continued for one hour at 80-90° C. and after cooling down, the resultant precipitate was filtered off and washed with ethanol to provide 0.6 g (16%) 1,1,2-trimethyl-3-phenyl-1H-benzo[e]indolium perchlorate as a yellow solid, which was sufficiently pure for the next synthetic step. $^1$H NMR (400 MHz, TFA) δ 8.05 (d, 1H, J=8.5), 7.86 (t, 2H, J=7.6), 7.62 (dd, 4H, J=6.8, 13.4), 7.52 (t, 1H, J=7.6), 7.37 (d, 2H, J=7.3), 7.00 (d, 1H, J=8.9), 2.58 (s, 3H), 1.81 (s, 6H).

1,1-Dimethyl-2-methylen-3-phenyl-2,3-dihydro-1H-benzo[e]indole

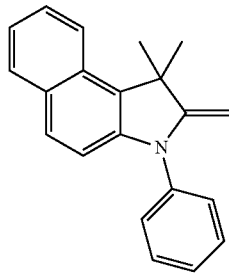 [SMILES: C=C1N(c2ccccc2)c2ccc3ccccc3c2C1(C)C]

1,1,2-Trimethyl-3-phenyl-1H-benzo[e]indolium perchlorate (11) (0.386 g) was suspended in 50 ml of benzene or diethyl ether and a solution 0.1 g potassium hydroxide in 2 ml water was added. The mixture was stirred at room temperature under nitrogen for one hour. The organic solvent layer was separated and washed with water and filtered through silica gel and then dried and evaporated. The resultant oily product (0.2 g) was sufficiently pure for the next synthetic step. $^1$H NMR (400 MHz, DMSO) δ 8.05 (d, 1H, J=8.5), 7.81 (d, 1H, J=8.1), 7.67 (d, 1H, J=8.8), 7.59 (t, 2H, J=7.8), 7.43 (dt, 4H, J=6.9, 20.3), 7.22 (t, 1H, J=7.3), 6.75 (d, 1H, J=8.7), 4.05 (d, 1H, J=1.7), 3.88 (d, 1H, J=1.7), 1.71 (s, 6H).

1,1,2-Trimethyl-3-phenyl-1H-benzo[e]indolium p-toluenesulfonate

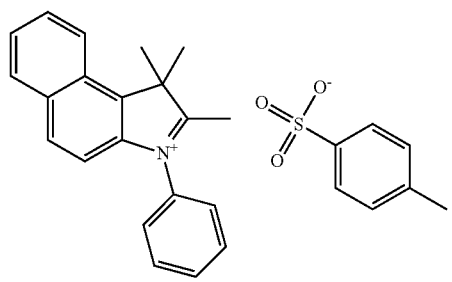 [SMILES: CC1=[N+](c2ccccc2)c2ccc3ccccc3c2C1(C)C ; Cc1ccc(S(=O)(=O)[O-])cc1]

1,1,2-Trimethyl-3-phenyl-1H-benzo[e] indolium perchlorate (3.86 g) was suspended in 50 ml of diethyl ether and a solution of 0.5 g sodium hydroxide in 5 ml water was added. The mixture was stirred at room temperature under nitrogen for half an hour. The ether layer was separated and washed with water and filtered through a thin layer of silica gel. To this solution 2 g of p-toluenesulfonic acid was added and the mixture stirred for an hour. The pink product was filtered off and washed with diethyl ether to provide 3.5 g (76%) 1,1,2-Trimethyl-3-phenyl-1H-benzo[e]indolium p-tolyenesulfonate, which was of sufficient purity to carry on to the next synthetic step. $^1$H NMR (400 MHz, TFA) δ 7.99 (d, 1H, J=8.5), 7.82 (m, 2H), 7.59 (m, 7H), 7.48 (t, 1H, J=7.6), 7.29 (m, 2H), 7.05 (t, 3H, J=9.2), 6.95 (d, 1H, J=9.0), 2.52 (s, 3H), 2.14 (s, 4H), 1.75 (s, 6H)

37

Sulfonated
1,1,2-Trimethyl-3-phenyl-1H-benzo[e]indolium

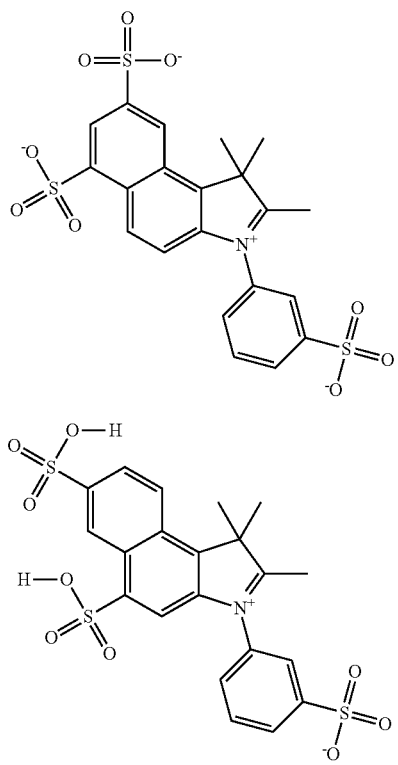

Fuming sulphuric acid (30%, 3 ml) was added at temperature below 0° C. to 1,1-dimethyl-2-methylen-3-phenyl-2,3-dihydro-1H-benzo[e]indole (0.57 g, 2 mmol) or 1,1,2-trimethyl-3-phenyl-1H-benzo[e]indolium p-tolyenesulfonate (0.9 g, 2 mmol) with cooling and stirred for 2 hours. The mixture was kept at room temperature for two hours and then heated at 80° C. for 12 hours. The solution was carefully diluted with dry diethyl ether and the oily product separated and washed with ether. Isomeric coupling partners CP-13A and CP-13B were separated by HPLC. Both compounds have strong fluorescence in water: CP-13A-green, CP-13B-blue.

Example XVI

38

This Example shows the preparation of exemplary compound Dye 5A and Dye 5B and their physical properties.

A mixture of appropriate 1,1,3-trimethyl-3-(3-sulfophenyl)-1H-benzo[e]indolium-disulfonate fraction (CP-13A or B), and 2-(4-carboxyphenyl)malonic aldehyde in a mixture of acetic anhydride and pyridine was heated at 120° C. for 15 minutes. The acetic anhydride was removed under reduced pressure and the product precipitated with ethylacetate.

Alternatively, a mixture of appropriate 1,1,3-trimethyl-3-(3-sulfophenyl)-1H-benzo[e] indolium-disulfonate fraction (CP-13A or B), and 2-(4-carboxyphenyl)malonic aldehyde dianil hydrochloride:

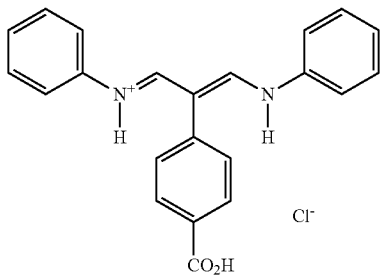 [SMILES: O=C(O)c1ccc(C(/C=[NH+]/c2ccccc2)=C\Nc2ccccc2)cc1 ; [Cl-]]

in a mixture of acetic anhydride and pyridine was heated at 120° C. for 5 min. The acetic anhydride was removed under reduced pressure. The product precipitated with ethylacetate and filtered off.

Figure 3:
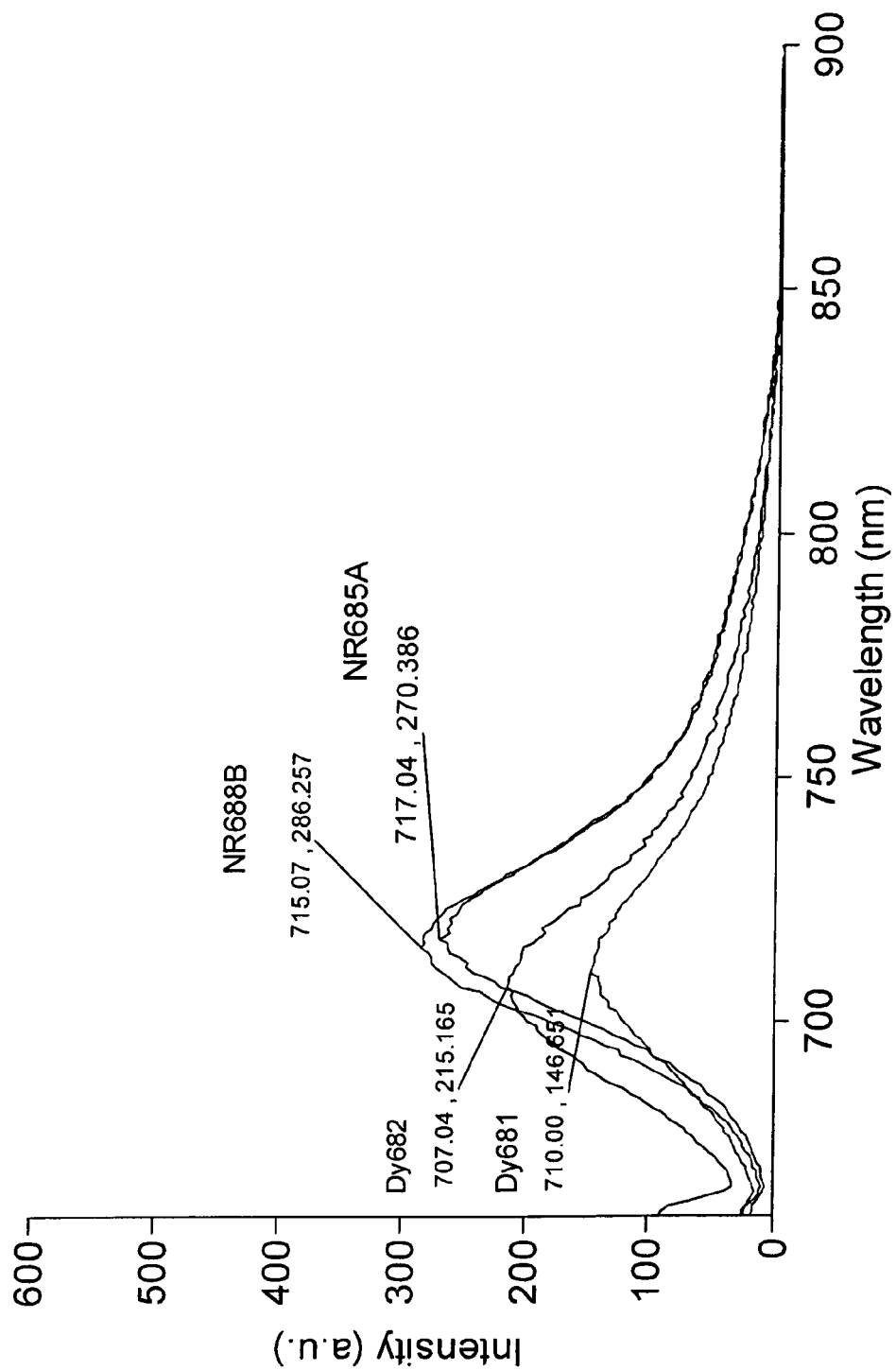
FIG. 3 shows a comparison of wavelength/fluorescence intensity of Dye 5A and 5B of the present invention with commercial dye Dy682.

Dye 5A, from CP-13A, has an absorption maximum at 686 nm in water and Dye 5B, from CP-13B, has an absorption maximum at 688 nm. A comparison of Dye 5A and 5B with commercially available Dy681 and Dy682 shows that the fluorescence intensity for Dye 5A and 5B are higher than the commercial dyes. Moreover, the fluorescence maximum for Dye 5A and 5B are red shifted and as a result providing better separation of the fluorescent signal from the excitation wavelength and less cross-talk with 660 dye. Finally, Dyes 5A and 5B are brighter than Dy681 and Dy681 and exhibit better stability as shown in FIG. 3.

Dye 5B

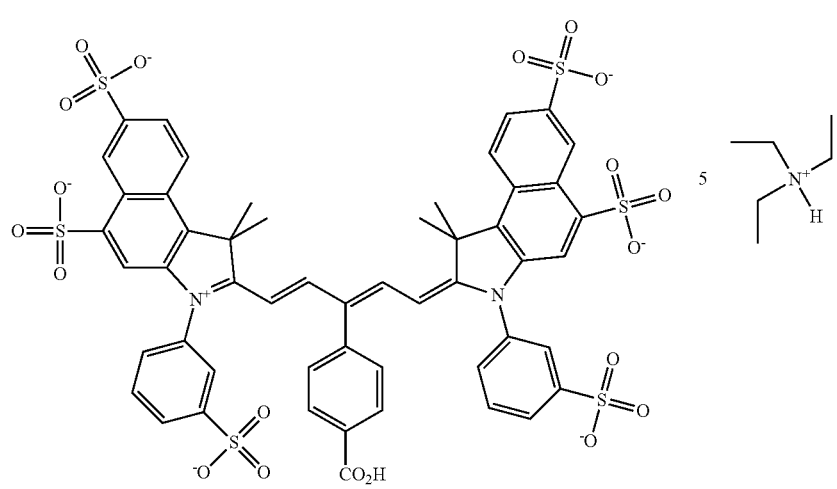

Example XVII

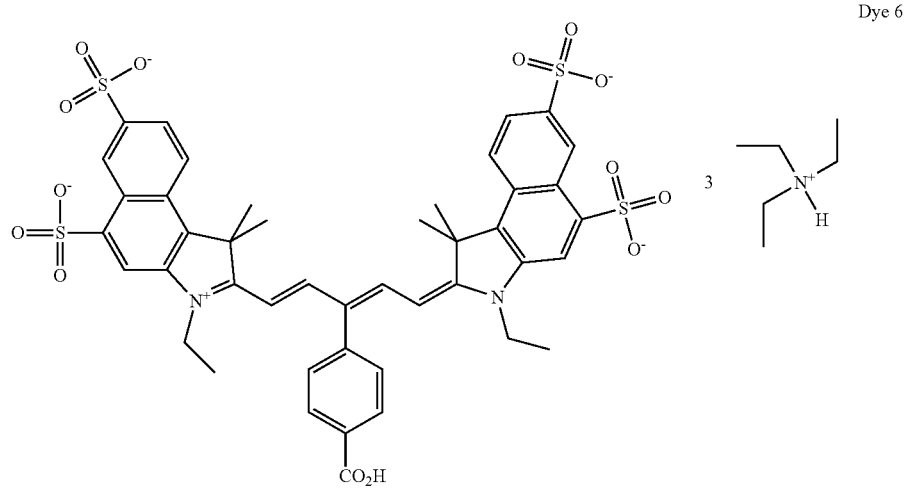

Dye 6

This Example shows the preparation of exemplary compound Dye 6 and its physical properties.

A mixture of appropriate 1,1,3-trimethyl-3-ethyl-7-sulfo-1H-benzo[e]indolium-5-sulfonate (CP-9, Example IX) and 2-(4-carboxyphenyl)malonic dialdehyde in acetic anhydride was heated at 140° C. for 5 min. The acetic anhydride was removed under reduced pressure and the product precipitated with ethylacetate.

Alternatively, for N-arylated analogues, a mixture of appropriate 1,1,3-trimethyl-3-(3-sulfophenyl)-1H-benzo[e]indolium-disulfonate fraction CP-13A or CP-13B, and 2-(4-carboxyphenyl)malonic aldehyde dianil hydrochloride in mixture of acetic anhydride and pyridine was heated at 120° C. for 5 min. Acetic anhydride removed under reduced pressure then product precipitated with ethylacetate and filtered off.

Dye 6 exhibited an absorption maximum at 673 nm in water. Dye 6 shows a higher relative fluorescence intensity.

Example XVIII

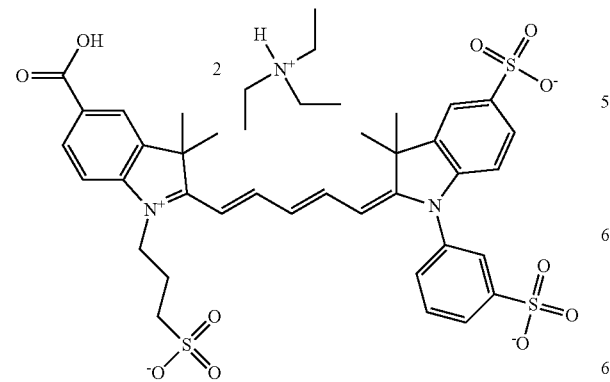

Dye 7

This Example shows the preparation of exemplary compound Dye 7 and its physical properties.

A mixture of 0.395 g (1 mmol) of 2,3,3-trimethyl-1-(3-sulfophenyl)-3H-indolium-5-sulfonate (CP-1, Example I) and 0.455 g (1 mmol) 2-(4-anilinobutadienyl)-3,3-dimethyl-5-carboxy-1-(3-sulfonatopropyl)-3H-indolium:

in 3 ml of acetic anhydride and 0.3 g triethylamine was heated for 20 minutes at 110° C. The acetic anhydride was removed under reduced pressure and the product precipitated with ethylacetate to provide 0.6 g (55%) of Dye7 which was purified by HPLC. Absorption max 650 nm (water). NR5-125 Abs.Max 650 nm

Example XIX

Dye 8

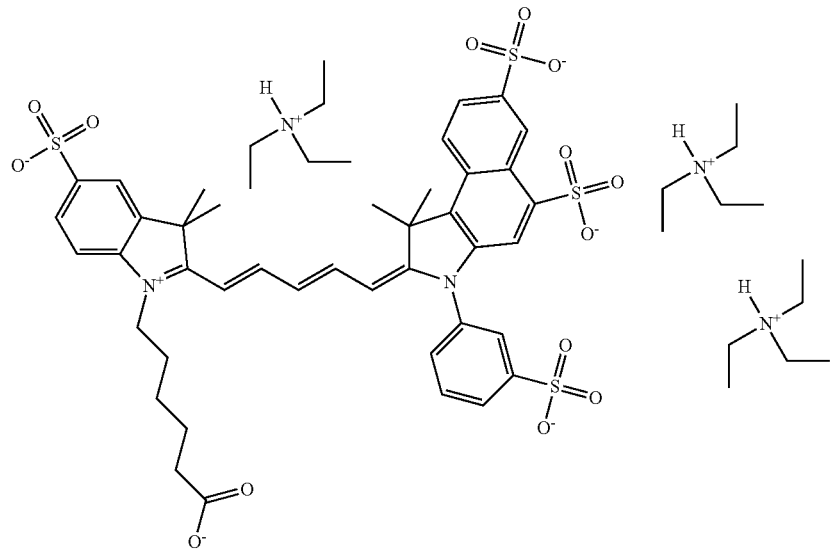

Molecular Weight = 911.02 3 102.20
Molecular Formula = C41H38N2O14S4 .3 C6H16N

A mixture of 1 mmol appropriate 1,1,3-trimethyl-3-(3-sulfophenyl)-1H-benzo[e]indolium-disulfonate fraction B (5B), and 0.525 g (1 mmol) 2-(4-acetanilidobytadienyl)-3,3-dimethyl-1-(5-carboxypentyl)-3H-indolium-5-sulfonate (3),

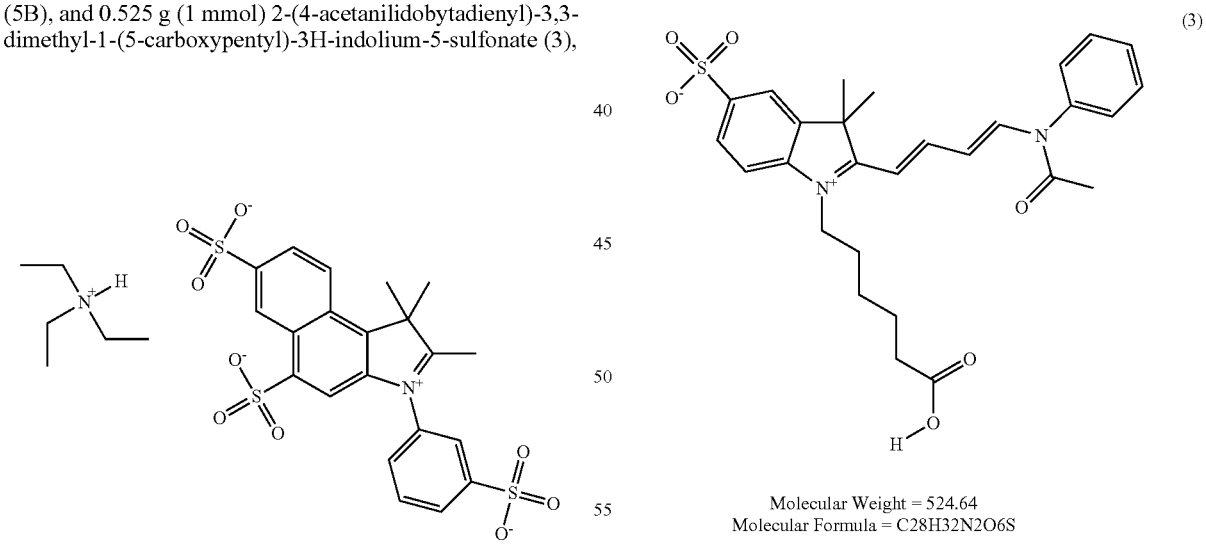

Molecular Weight = 523.56 2 102.20
Molecular Formula = C21H17NO9S3 . 2 C6H16N

Molecular Weight = 524.64
Molecular Formula = C28H32N2O6S 3 ml of acetic anhydride and 0.3 g triethylamine was heated 20 minutes at 110° C. Acetic anhydride removed under reduced pressure then product precipitated with ethylacetate. Yield 0.6 g (55%). Product was purified by HPLC. Absorption max 664 nm (water). Fluorescence max 687 nm (water). This new dye (NR665) has more than 3 times stronger fluorescence in water compare with Dy681

Example XX

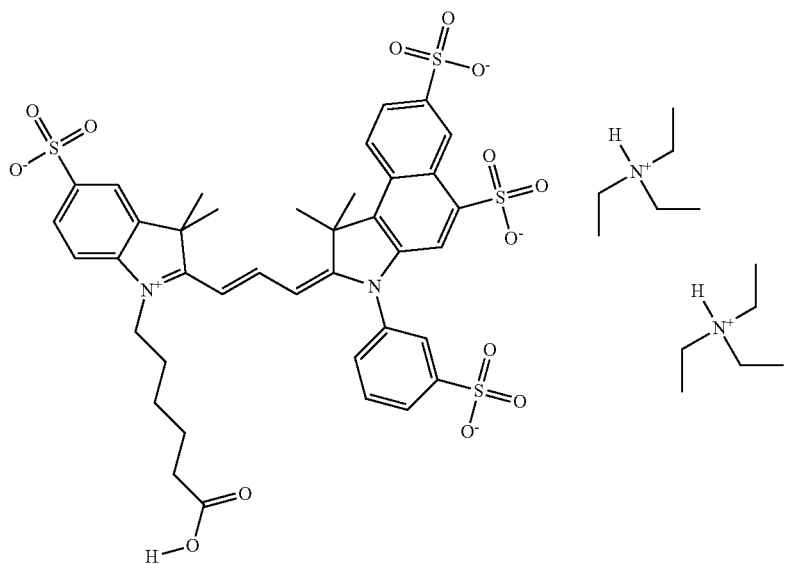

Molecular Weight = 855.9 2 102.20
Molecular Formula = C39H37N2O14S4 .2 C6H16N

A mixture of 1 mmol appropriate 1,1,3-trimethyl-3-(3-sulfophenyl)-1H-benzo[e]indolium-disulfonate fraction B (5B), and 0.525 g (1 mmol) 2-(4-acetanilidobytadienyl)-3,3-dimethyl-1-(5-carboxypentyl)-3H-indolium-5-sulfonate (3),

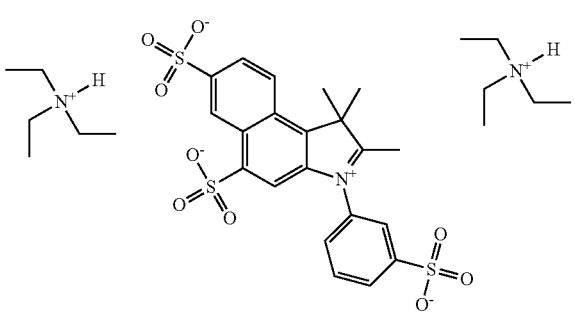

Molecular Weight = 523.56 2 102.20
Molecular Formula = C21H17NO9S3 .2 C6H16N

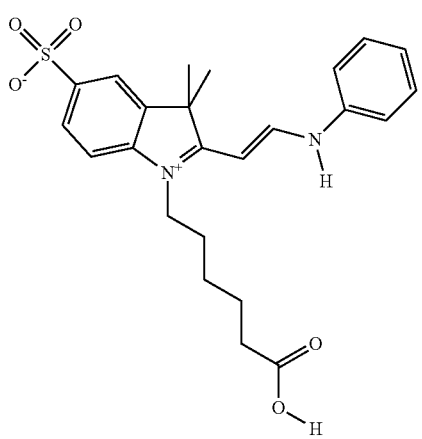

Molecular Weight = 456.57
Molecular Formula = C24H28N2O5S 3 ml of acetic anhydride and 0.3 g triethylamine was heated 20 minutes at 110° C. Acetic anhydride removed under reduced pressure then product precipitated with ethylacetate. Yield 45%. Product was purified by flash-column. Absorption max 567 nm (water).

A few examples of symmetrical N-phenyl-substituted indocyanine dyes are known such as dyes 1, 2

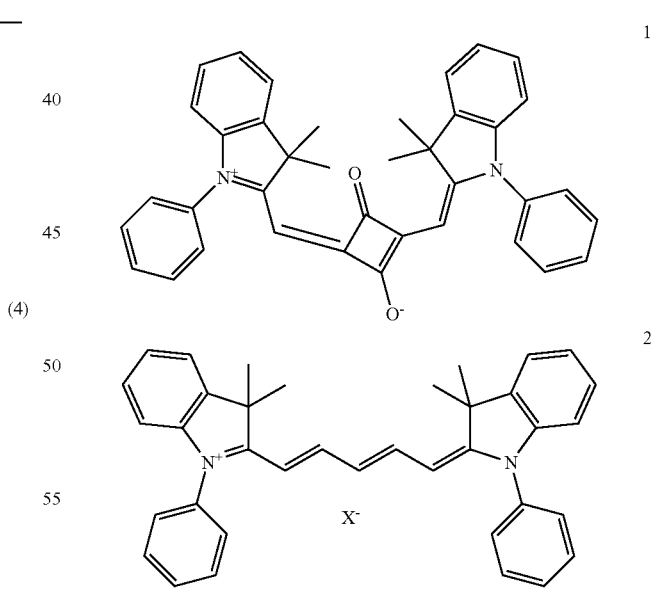

see for example: EP 1134613 (2001); US 2005/0013966, JP 2002226731. These dyes have fluorescence properties and therefore they found some practical application: WO 96/10620; US 2004/6835431. However, such dyes can have insufficient fluorescence in water or biological systems. To compare fluorescent properties of dyes based on unknown before sulfonated N-arylindole derivatives and known prototype (2) some new dye with one (NR 647 S1) and t(NR 647 S2)N-phenyl-indole moiety were prepared.

Spectral properties for solutions of new symmetrical dyes in water presented in Table 1.

TABLE 1

| Dye | $R_1$ | $R_2$ | Absorption max, nm | Fluorescence max, nm | Fluorescence intensity, % |
|---|---|---|---|---|---|
| S0 (2) | H | H | 649 | 674 | 100 |
| S1 | $SO_3^-$ | H | 653 | 676 | 170 |
| S2 | $SO_3^-$ | $SO_3^-$ | 653 | 676 | 190 |

The family of indocyanine dyes based on new starting materials—sulfonated N-aryl-indole derivatives have significantly stronger fluorescence (up to two times).

Further investigations reveal that solutions of new dyes (such as NR647 S2 and NR647 S1) not only have stronger fluorescence but they are more photo-stable than prototype (2) as well. One of the modern applications of cyanine dyes based on their fluorescent properties is chemically labelling of different bio-molecules. For such applications a dye molecule can be modified with a functional group like amino or carboxy-groups, which making them suitable for coupling. For this purpose a series of unsymmetrical dyes with one functional carboxy- and at least one sulfonic group have been prepared.

Table 2 shows the fluorescence properties of unsymmetrical N-arylindodicarbocyanines in water.

TABLE 2

| Dye | R1 | R2 | Absorption max, nm | Fluorescence max, nm | Fluorescence intensity, % |
|---|---|---|---|---|---|
| NR 647-0 | H | H | 648 | 670 | 100 |
| NR 647-1 | SO3- | H | 649 | 672 | 125 |
| NR 647-2 | SO3- | SO3- | 648 | 670 | 120 |

This family of unsymmetrical indocyanine dyes based on new starting materials—sulfonated N-aryl-indole derivatives have quite strong fluorescence and they can be useful for different applications, which are using fluorescent dyes chemically conjugated to different bio-molecules. The present invention provides dyes that have improved fluorescent properties compared to various commercial dyes such as Cy3, Cy5, and Alexa647 for the same spectral region Example XXI This Example shows the preparation of Dye 9.

Dye structure 9 has been prepared in accordance with embodiments disclosed herein. Some details provided below

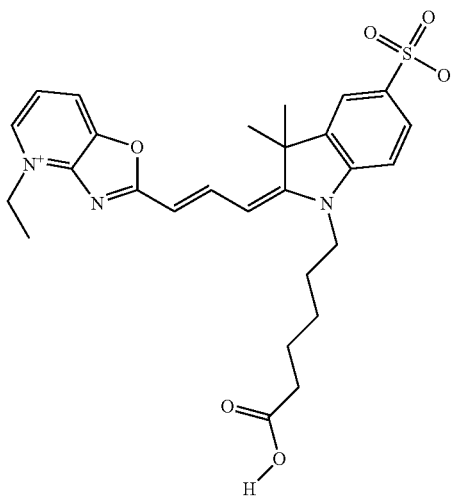

This Example shows the preparation of exemplary compound Dye 9 and its physical properties. A mixture of 1.34 g (10 mmol) 2-methyl-oxazolo[4,5-b]pyridine and 2 ml ethyliodide in a closed system was kept 2 h at 110° C. The product was precipitated with acetone and filtered off. The yellow crystalline product was filtered off and washed with diethyl ether to provide 2.47 g (86%) 4-ethyl-2-methyl-oxazolo[4,5-b]pyridinium iodide, which was of sufficient purity to carry on to the next synthetic step.

A mixture of 0.29 g (1 mmol) 4-ethyl-2-methyl-oxazolo[4,5-b]pyridinium iodide and 0.2 ml ethylisoformalilide was kept 1 h at 100° C. The product was precipitated with ether and filtered off. The crystalline product was filtered off and washed with diethyl ether to provide 0.3 g (76%) 4-ethyl-2-(2-phenylamino)vinyl-oxazolo[4,5-b]pyridinium iodide, which was of sufficient purity to carry on to the next step of dye synthesis.

Dye 9. Method A

A mixture of 0.29 g (1 mmol) of 4-ethyl-2-methyl-oxazolo[4,5-b]pyridinium iodide, 0.457 g (1 mmol) 2-(2-anilinovinyl)-3,3-dimethyl-1-(5-carboxypentyl)-3H-indolium-5-sulfonate:

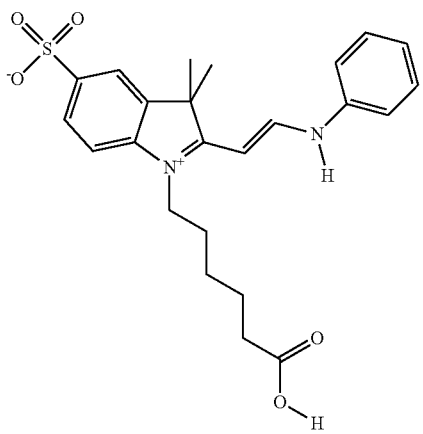

3 ml of acetic anhydride and 0.3 g triethylamine were heated 20 minutes at 110° C., acetic anhydride-removed under reduced pressure then the product precipitated with diethyl ether. The product was purified by HPLC. The absorption maximum of equimolar solutions in ScanMix of new dye 9 was 536 nm, 0.162 a.u.

Dye 9. Method B

A mixture of 0.39 g (1 mmol) of 4-ethyl-2-(2-anilino)vinyl-oxazolo[4,5-b]pyridinium iodide, 0.35 g (1 mmol) 2,3,3-trimethyl-1-(5-carboxypentyl)-3H-indolium-5-sulfonate, 3 ml of acetic anhydride and 0.13 g of sodium acetate was heated 20 minutes at 110° C. Acetic anhydride was removed under reduced pressure then the product precipitated with diethyl ether. The product was purified by flash column. Spectral properties investigation of dye 9 revealed that this representative of unsymmetrical indocyanine dyes has an absorption maximum at about 536 nm closer to the laser excitation wavelength (532 nm). This new dye 9 (max 583 nm, 447 a.u.) has stronger fluorescence compared with DG527 (594 nm, 401 a.u.).

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A compound of formula I or mesomers thereof:

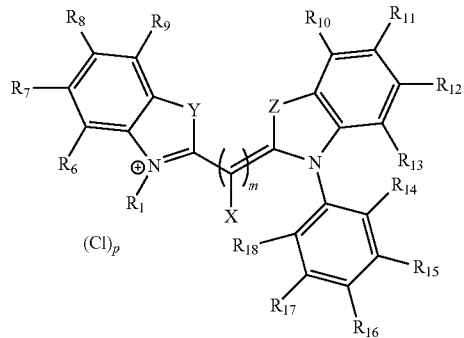

wherein

Cl is a charge balancing counterion and p is an integer from 1-7;

m is 1, 3, 5, 7, or 9;

each incidence of X is independently hydrogen, halogen, alkyl- or aryloxy, alkyl- or arylthio, amino- or substituted amino, aryl or alkyl, any of which may be optionally substituted with a substituent selected from carboxyl, sulfonate, sulfinate, sulfonamide, hydroxyl, amino, alkyl- or aryl- amino, dialkyl(aryl)amino, alkoxy, aryloxy, alkyl- or arylthio and halogen; optionally, one or more X groups are combined to form a cyclic ring;

Y is independently selected from O, $NR_a$, S, Se, $CR_b=CR_c$ or $CR_2R_3$;

Z is independently selected from O, $NR_a$, S, Se, $CR_b=CR_c$ or $CR_4R_5$;

wherein $R_a$, $R_b$, $R_c$, $R_2$, $R_3$, $R_4$, and $R_5$ are independently selected from hydrogen, halogen, alkyl- or aryloxy, alkyl- or arylthio, amino- or substituted amino, alkyl, aryl or substituted alkyl, or substituted aryl;

$R_1$ is selected from aryl or alkyl, any of which may be optionally substituted with at least one substituent selected from carboxyl, sulfonate, sulfinate, sulfonamide or substituted sulfonamide, hydroxyl, amino, alkyl(aryl)amino, dialkyl(aryl)amino, alkoxy, halogen, succinimidyl ester, ester, and amide or substituted amide;

$R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ are independently selected from carboxyl, sulfonate, sulfinate, sulfoxide, sulfone, sulfonamide, hydroxyl, amino, alkylamino, dialkylamino, alkoxy, halogen, alkyl succinimidyl ester, ester, amide, or any ortho-disposed pair of $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ is combined to form a further fused aromatic or heterocyclic ring that is optionally substituted; wherein at least one of $R_{14}$, $R_{15}$, $R_{16}$, $R_{17}$, or $R_{18}$ is sulfonate or a further fused ring derived from $R_{14}$, $R_{15}$, $R_{16}$, $R_{17}$, or $R_{18}$ comprises at least one sulfonate substituent; with the proviso that none of $R_{14}$, $R_{15}$, $R_{16}$, $R_{17}$, and $R_{18}$ are carboxyl and wherein provided that Y is $CR_2R_3$ or Z is $CR_4R_5$.

2. The compound of claim 1 having the structure IA or mesomer thereof:

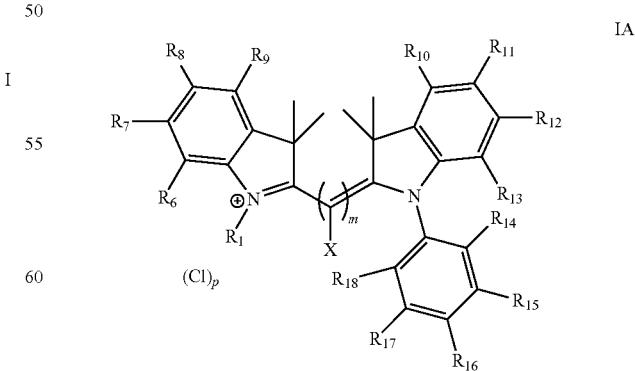

3. The compound of claim 1 having the structure IB or mesomer thereof:

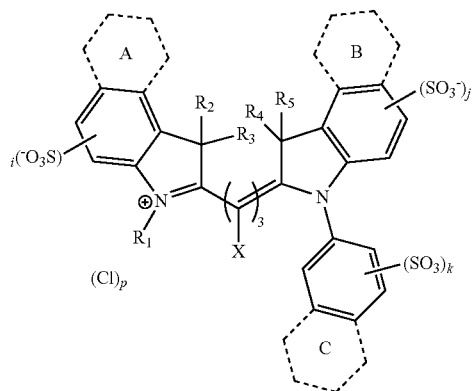

IB wherein i and j are, independently, 0, 1, or 2; k is 1 or 2; and A, B, and C are independently, optional further ring fusion.

4. The compound of claim 1 having the structure IC or mesomer thereof:

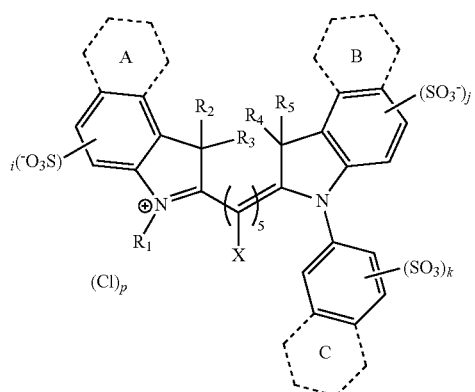

IC wherein i and j are, independently, 0, 1, or 2; k is 1 or 2; and A, B, and C are independently, optional further ring fusion.

5. The compound of claim 1 having the structure ID or mesomer thereof:

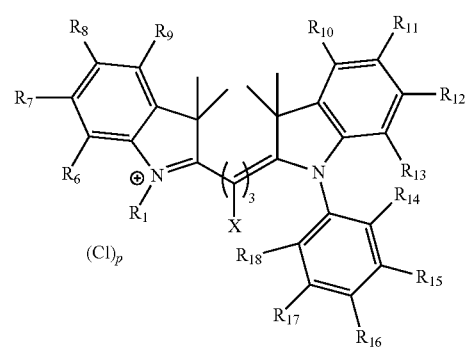

ID

6. The compound of claim 5 having the structure ID1 or mesomer thereof:

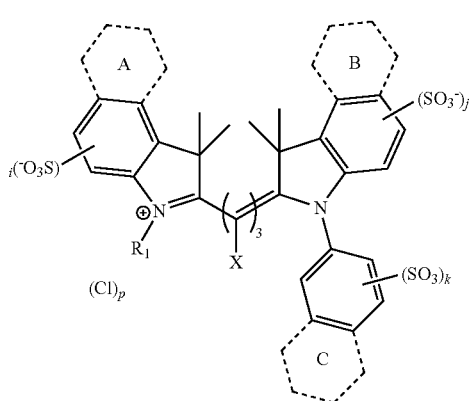

ID1 wherein i and j are, independently, 0, 1, or 2; k is 1 or 2; and A, B, and C are independently, optional further ring fusion.

7. The compound of claim 1 having the structure IE or mesomer thereof:

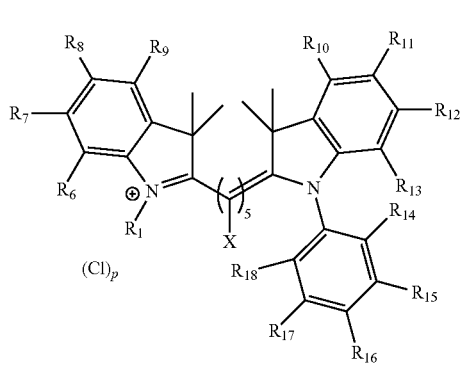

IE

8. The compound of claim 7 having the structure IE1 or mesomer thereof:

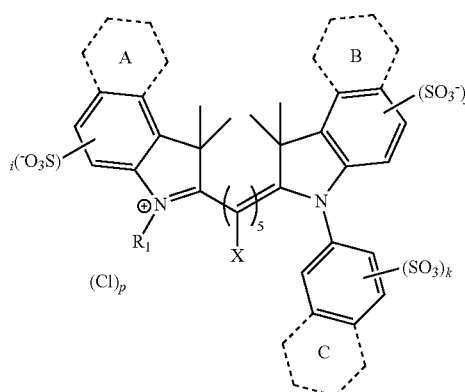

IE1 wherein i and j are, independently, 0, 1, or 2; k is 1 or 2; and A, B, and C are independently, optional further ring fusion.

9. The compound of claim 1 selected from:
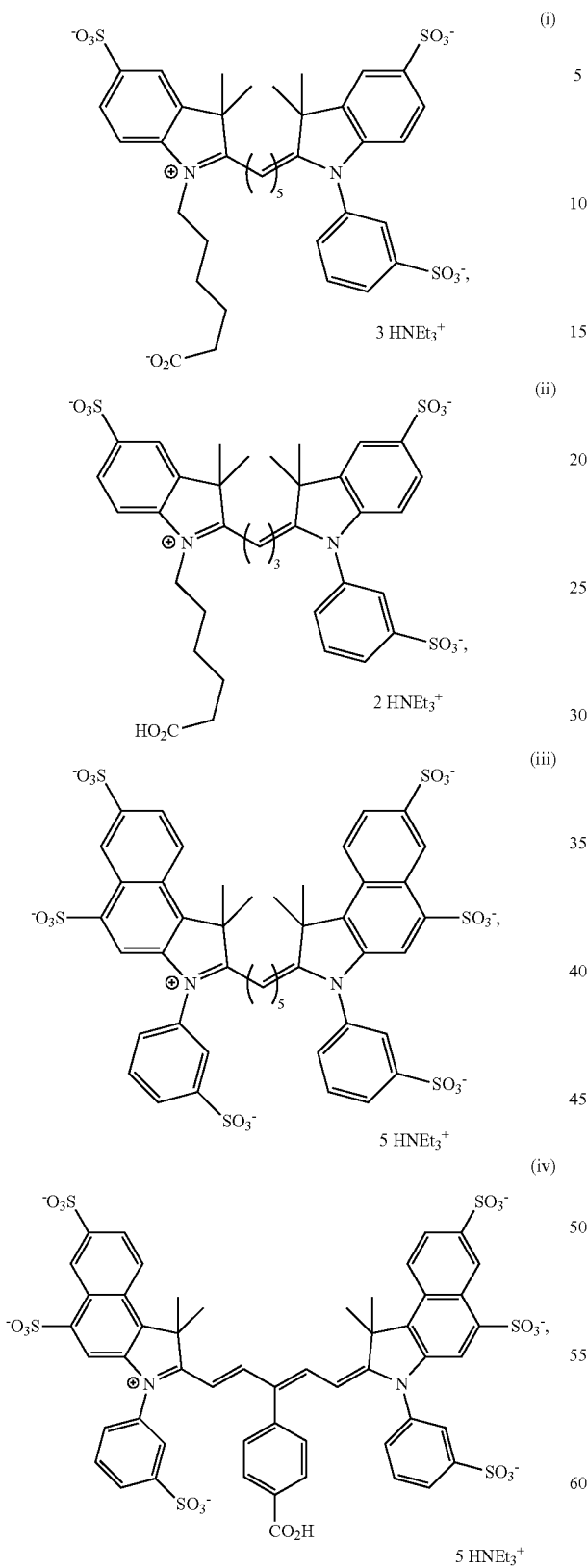
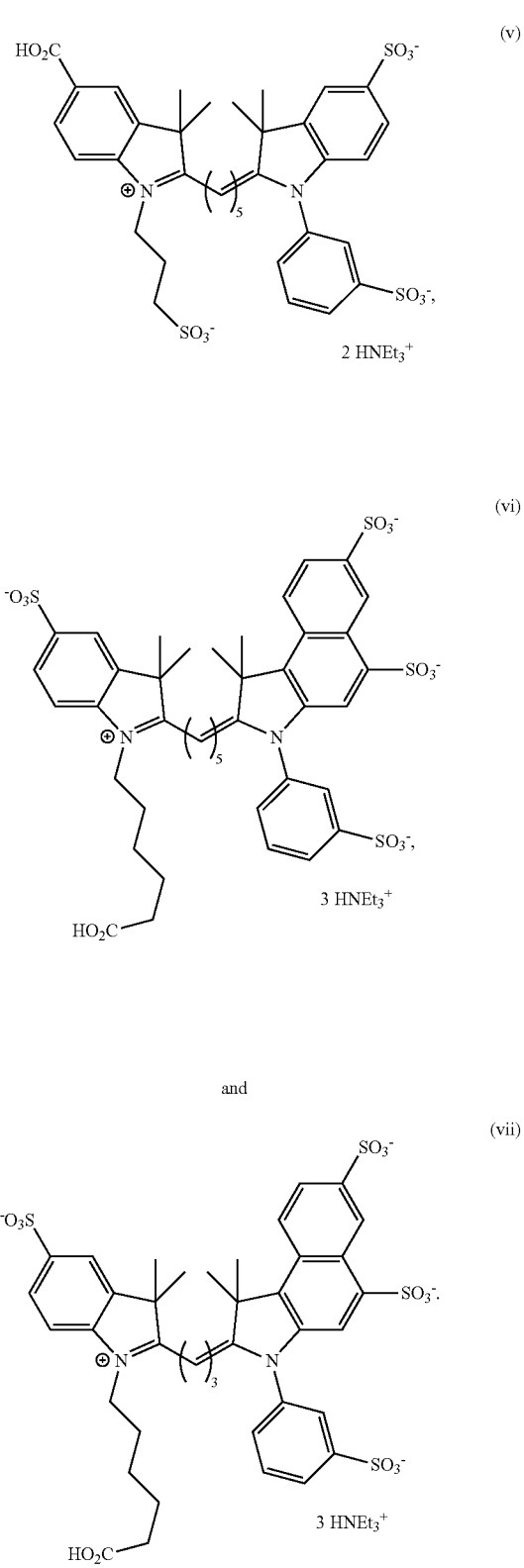
* * * * *